United States Patent
Duckett et al.

(10) Patent No.: US 11,389,551 B2
(45) Date of Patent: Jul. 19, 2022

(54) POLARISATION TRANSFER VIA A SECOND METAL COMPLEX

(71) Applicant: University of York, York (GB)

(72) Inventors: Simon Duckett, North Yorkshire (GB); Soumya Singha Roy, North Yorkshire (GB); Kate M. Appleby, Midlothian (GB)

(73) Assignee: UNIVERSITY OF YORK

( * ) Notice: Subject to any disclaimer, the term of this patent is extended or adjusted under 35 U.S.C. 154(b) by 246 days.

(21) Appl. No.: 16/627,713

(22) PCT Filed: Jul. 3, 2018

(86) PCT No.: PCT/GB2018/000103
§ 371 (c)(1),
(2) Date: Dec. 30, 2019

(87) PCT Pub. No.: WO2019/008308
PCT Pub. Date: Jan. 10, 2019

(65) Prior Publication Data
US 2021/0154333 A1    May 27, 2021

(30) Foreign Application Priority Data
Jul. 3, 2017    (GB) .................................. 1710677

(51) Int. Cl.
*A61K 49/10* (2006.01)
*C07F 15/00* (2006.01)
*G01R 33/28* (2006.01)
*G01R 33/56* (2006.01)

(52) U.S. Cl.
CPC .......... *A61K 49/106* (2013.01); *A61K 49/103* (2013.01); *C07F 15/0093* (2013.01); *G01R 33/282* (2013.01); *G01R 33/5601* (2013.01); *G01R 33/5605* (2013.01)

(58) Field of Classification Search
CPC ............ A61K 49/106; A61K 49/103; G01R 33/5605; G01R 33/5601; G01R 33/282; C07F 15/0093
See application file for complete search history.

(56) References Cited

U.S. PATENT DOCUMENTS

| 2011/0274626 A1* | 11/2011 | Duckett | ................ C07F 15/004 424/9.361 |
| 2016/0169998 A1* | 6/2016 | Warren | ................ G01R 33/445 324/309 |

FOREIGN PATENT DOCUMENTS

| WO | 99/35508 A1 | 7/1999 |
| WO | 2010/037771 A1 | 4/2010 |
| WO | 2016/038013 A1 | 3/2016 |

OTHER PUBLICATIONS

Wissam Iali et al.; "Achieving High Levels of NMR-Hyperpolarization in Aqueous Media With Minimal Catalyst Contamination Using SABRE"; Chemistry—A European Journal; vol. 23; (2017); pp. 10491-10495.
Andreas Koch et al.; "Examination of subsequent reaction products enhanced through parahydrogen-induced nuclear polarization (PHIP)"; Magnetic Resonance in Chemistry; vol. 38; (2000;) pp. 216-220.
S.J. Kohler et al.; "In Vivo 13Carbon Metabolic Imaging at 3T With Hyperpolarized 13C-1-Pyruvate"; Magnetic Resonance in Medicine; vol. 58; (2000); pp. 65-69.
Soumya S. Roy et al.; "SABRE-Relay: A Versatile Route to Hyperpolarization"; Journal of Physical Chemistry Letters; vol. 9, (2018); pp. 1112-1117.
PCT International Search Report and PCT Written Opinion for PCT International Patent Application No. PCT/GB2018/000103; dated Nov. 6, 2018; (22 pages).

* cited by examiner

*Primary Examiner* — Michael G. Hartley
*Assistant Examiner* — Leah H Schlientz
(74) *Attorney, Agent, or Firm* — K&L Gates LLP

(57) ABSTRACT

There is described a method for preparation of an imaging medium via transfer from a hyperpolarised singlet state that is not parahydrogen, said method comprising the steps of: (i) preparing a system containing: parahydrogen; a magnetisation transfer complex, with a molecular symmetry that allows the creation of a singlet state between spin pairs within it, said complex including a reversibly bound small molecule transference substrate; applying a magnetic field such that hyperpolarisation is transferred into the transfer complex, including the reversibly bound small molecule transference substrate; (ii) introducing a recipient complex capable of binding the small molecule transference substrate, said recipient complex including a recipient substrate, such that the recipient complex and recipient substrate, including the bound transference substrate, is hyperpolarised.

22 Claims, 10 Drawing Sheets

POLARISATION TRANSFER VIA A SECOND METAL COMPLEX

CROSS REFERENCE TO RELATED APPLICATIONS

This is the national phase under 35 U.S.C. § 371 of International Application No. PCT/GB2018/000103, filed on Jul. 3, 2018, which claims priority to and the benefit of United Kingdom Patent Application No. 1710677.4 filed on Jul. 3, 2017, the entire disclosures of each of which are incorporated by reference herein.

FIELD OF THE INVENTION

The present invention relates to a method for the production of a hyperpolarised agent via transfer from a hyperpolarised singlet state that is not parahydrogen.

More particularly, the present invention provides a method for the production of a hyperpolarised agent by transferring a ligand possessing a hyperpolarised singlet state from a first hyperpolarised complex, e.g. a hyperpolarised metal complex; to a second complex, e.g. second metal complex.

The present invention also provides an imaging medium, a method of preparation of said imaging medium and a method for carrying out an MR experiment, e.g. NMR or MRI, with enhanced sensitivity on a metal complex or a ligand that might otherwise be difficult to hyperpolarise.

BACKGROUND OF THE INVENTION

NMR is commonly used across a large number of disciplines, including chemistry, biochemistry and medicine, and is inherently insensitive as it probes a population difference between states that are close in energy. This population difference can be increased by employing a hyperpolarization technique, such as optical pumping, dynamic nuclear polarisation (DNP)[1] or the use of parahydrogen (p-$H_2$)[2], via parahydrogen induced polarization (PHIP)[3], to increase sensitivity.

Magnetic resonance imaging (MRI) is a technique based upon the science of nuclear magnetic resonance (NMR). MRI has become particularly attractive to physicians as images of parts of a patient's body thereof can be obtained non-invasively and without exposing the patient and the medical personnel to potentially harmful radiation such as X-rays.

Furthermore, due to its high quality images and good spatial and temporal resolution, MRI is a favourable imaging technique for imaging patients' soft tissue and organs.

Signal amplification by reversible exchange (SABRE) is a technique which increases the response (or visibility) of compounds in NMR and MRI measurements. This increased visibility allows higher contrast and resolution MRI imaging, shorter scan times and lower detection thresholds in NMR spectroscopy. Unlike other polarisation methods, such as DNP, the SABRE process can be performed in seconds, and the agents are then measured using NMR or MRI.

One of the main advantages of SABRE is that it achieves this result without the incorporation of p-$H_2$ into the substrate. This technique is effectively a form of catalysis which utilizes a suitable catalyst[4], to reversibly bind both $H_2$ (p-$H_2$) and the substrate in order to assemble a reaction intermediate in which polarization is able to transfer, at low magnetic fields, from p-$H_2$ into the substrate.[5]

NMR and MRI involve the detection of what can be viewed to be transitions of nuclear spins between an excited state and a ground state in an applied magnetic field. Because the energy difference between these states is relatively small, the usual Boltzmann distribution of chemically identical nuclei is such that at room temperature the populations of nuclear spin states which are in dynamic equilibrium are almost identical. Since the strength of the detected signal in magnetic resonance experiments is proportional to the population difference, NMR and MRI signals are typically weak.

The strength of detectable NMR signals can however be enhanced by hyperpolarizing the magnetic nuclei. Hyperpolarization in this context refers to a process in which a significant excess of magnetic nuclei are induced into a spin state. This results in a large increase in available signal due to the much larger inequality of populations across the energy levels that will ultimately be probed. In order for a hyperpolarised state to be useful, it is important that the spin state is sufficiently long lived to provide useful information, i.e. that the relaxation time of the spin state is 'long'. The rules governing the relaxation rates of nuclear spins are complex but known. It suffices to say that certain nuclei and spins systems have relaxation times which may extend from seconds to hours, days, months or even years.

There are a number of ways to induce certain nuclei into a hyperpolarised state. The simplest way is to cool the material to very low temperatures in the presence of a magnetic field, which will favour population of the lower energy state in which the spins of the nuclei are aligned with the applied magnetic field. This method is suitable for the production of hyperpolarised monatomic gases such as xenon or helium-3. The polarization levels of these nuclei have also been increased via the use of laser-based technologies.

One important objective of hyperpolarization lies in the area of magnetic resonance imaging (MRI) where applications in medical diagnosis are expected.[6] In fact, biomedical applications such as tumour or metabolic-flux imaging, in vivo, are beginning to become a reality for the resulting hyperpolarised agents.[7] Consequently, the toxicity of the SABRE catalyst, solvent and substrate combination need to be minimized if this method is ever to find clinical use.

Nuclei can be hyperpolarised by a process known as parahydrogen induced polarization (PHIP). PHIP has proved to be highly efficient and has currently achieved greater enhancement of heteronuclear NMR signals than other methods known in the art. PHIP is generally the result of a chemical reaction in which the parahydrogen nuclei are transferred irreversibly into another molecule having certain symmetry properties. Under the right circumstances, the spin state of the parahydrogen molecule is preserved in the spins of the two hydrogen atoms which become part of the new molecule. If other NMR-active nuclei are within coupling distance of the hydrogen nuclei, spin polarization of those nuclei can be transferred spontaneously in an optimal magnetic field. In this way, the signals of heteronuclei such as $^{13}C$, $^{15}N$ and $^{31}P$ can be enhanced. By way of example, WO 99/24080 describes a PHIP process in which parahydrogen is added across a symmetrical carbon-carbon double bond containing a $^{13}C$ centre. In one example of such a process, Wilkinson's catalyst is first reduced by addition of parahydrogen, followed by addition of an ethylene ligand. The resulting hydride ligands then undergo a migratory insertion reaction with the ethylene ligand, which subsequently dissociates from the complex to form uncoordinated hyperpolarised ethane. An overview of PHIP is given in Duckett et al, Accounts Chemical Research 2012, 1247-1257.

Conventional PHIP processes therefore involve the chemical addition of parahydrogen to hydrogenatable substrates (compounds), usually organic substrates (compounds) containing double and triple bonds. These processes are therefore limited to substrates (compounds) capable of undergoing hydrogenation. Furthermore, hydrogen equivalence is not preserved at all stages, which leads to some loss of hyperpolarization through relaxation.

Currently the best reported catalyst for SABRE is [IrCl (COD)(IMes)][8], delivering $^1$H-signal enhancements of up to 4000 fold in methanol-$d_4$ solution where there is both high catalyst and p-$H_2$ solubility. While previous studies have shown that less toxic ethanol-$d_6$/$D_2O$ mixtures can be employed, the level of signal gain is typically reduced.[9] Feiters et al, prepared a water soluble catalyst for use with SABRE but the resulting enhancements in water were again weak when compared to those in methanol.[10] Others have further modified this approach but low activity has proven to be a common issue.[11]

International Patent application No. WO 99/35508 discloses a method of MR investigation of a patient using a hyperpolarised solution of a high $T_1$ agent as MR imaging agent. When using a hyperpolarised $^{13}$C- and/or $^{15}$N-enriched high $T_1$ agent, there will be essentially no interference from background signals as the natural abundance of $^{13}$C and/or $^{15}$N is negligible and thus the image contrast will be advantageously high. A variety of possible high $T_1$ agents suitable for hyperpolarisation and subsequent use as MR imaging agents are disclosed including but not limited to non-endogenous and endogenous compounds like acetate, pyruvate, oxalate or gluconate, sugars like glucose or fructose, urea, amides, amino acids like glutamate, glycine, cysteine or aspartate, nucleotides, vitamins like ascorbic acid, penicillin derivatives and sulfonamides. In a particular aspect of the present invention the recipient substrate is pyruvate. It is further stated that intermediates in normal metabolic cycles such as the citric acid cycle like fumaric acid and pyruvic acid are preferred imaging agents for the imaging of metabolic activity.

However, the signal of a hyperpolarised imaging agent decays due to relaxation and due to dilution upon administration to a patient. Hence the $T_1$ value of an imaging agent in biological fluids (e.g. blood) must be sufficiently high to enable the agent to be distributed to a target site in the patient's body in a highly hyperpolarised state.

The NMR signal enhancements gained using the SABRE technique are currently limited to resonances corresponding to nuclei on ligands that bind reversibly to iridium, which are typically N-heterocycles. Polarisation has also been observed to transfer, via J coupling, onto the 'scaffolding' of the iridium complexes, i.e.—the ligands that stabilise the iridium and are fixed in place. These are typically N-heterocyclic carbenes or phosphines.

US Patent application No. 2015/0064113 describes a method of preparing an MRI contrast agent which comprises providing a molecule comprising at least four non-zero-spin nuclei, and wherein the molecule is selected from the group consisting of diphenylacetylene and diethyl oxalate; hyperpolarising the molecule and applying radiofrequency pulses to the hyperpolarised molecule.

US Patent application No. 2016/0169998 describes a method for nuclear spin polarization enhancement via signal amplification by reversible exchange at very low magnetic fields. The method described therein comprises combining parahydrogen, a compound comprising at least one hyperpolarisable heteronucleus and a catalyst to form a mixture and applying a magnetic field to the mixture thereby transferring the sin order from parahydrogen to the hyperpolarisable heteronucleus. However, the hyperpolarisation does not transfer from one hyperpolarised compound to another.

To further generalise the use of SABRE, we have investigated its potential to work alongside other metal complexes. The aim is to polarise a ligand at iridium, e.g. via PHIP. This polarised ligand may then dissociate from the iridium centre and bind to the metal centre of another complex. The polarisation remaining on the ligand can then transfer via J coupling to the 'scaffolding' of the second complex, thus enhancing the NMR resonances of the second metal complex. Furthermore, polarisation enhancements are observed for the unbound ligands in solution, as well as the ligands bound to iridium.

SUMMARY OF THE INVENTION

Thus, according to a first aspect of the invention there is provided a method for the preparation of an imaging medium via transfer from a hyperpolarised singlet state that is not parahydrogen, said method comprising the steps of:
(i) preparing a system containing:
parahydrogen; a magnetisation transfer complex, with a molecular symmetry that allows the creation of a singlet state between spin pairs within it, said complex including a reversibly bound small molecule transference substrate;
applying a magnetic field such that hyperpolarisation is transferred into the transfer complex, including the reversibly bound small molecule transference substrate;
(ii) separately or simultaneously introducing a recipient complex capable of binding the small molecule transference substrate, said recipient complex including a recipient substrate, such that the recipient complex and recipient substrate, including the bound transference substrate, is hyperpolarised; and
(iii) providing an imaging medium by:
(a) separating the hyperpolarised recipient complex;
(b) separating the hyperpolarised recipient substrate; or
(c) separating the transference substrate.

Although the hyperpolarisation can be achieved by SABRE, it will be understood that other methods of hyperpolarisation may suitably be applied.

There are a number of ways to induce certain nuclei into a hyperpolarised state. The simplest way is to cool the material to very low temperatures in the presence of a magnetic field, which will favour population of the lower energy state in which the spins of the nuclei are aligned with the applied magnetic field. This method is suitable for the production of hyperpolarized monatomic gases such as xenon or helium-3. The polarization levels of these nuclei have also been increased via the use of laser-based technologies.

Thus, for example, the hyperpolarisation may be achieved by polarisation transfer from a noble gas, spin refrigeration, DNP, para-hydrogen induced polarization (PHIP) and SABRE. However, in one particular aspect of the invention the hyperpolarisation is introduced by SABRE and thus, the magnetisation transfer complex is a (SABRE) magnetisation transfer complex.

In SABRE, a catalyst reversibly binds p-$H_2$ and the substrate to transfer dormant spin order from p-$H_2$ into the substrate via a scalar-coupling framework.

This resulting singlet state of the small molecule transference substrate will desirably be characterised by a long lifetime in a low magnetic field. Preferably, the resulting singlet state lifetime will be 20 seconds or more, preferably more than 20 seconds or more than 25 seconds or more than 30 seconds. The resulting singlet state lifetime may last one or more minutes.

When SABRE is utilised as the method of hyperpolarisation, a SABRE hyperpolarisation transfer catalyst (e.g. [IrCl(COD)IMes] or a $^2$H-labelled counterpart or a catalyst may be added to optimise the process in a non-aqueous phase with the selected singlet state derived agent. An appropriate singlet state derived agent and/or a SABRE hyperpolarisation transfer catalyst may optionally be placed in the aqueous phase.

$H_2$ or parahydrogen (p-$H_2$) gas may be added to the resulting system whilst agitating the system to activate the catalyst through stirring, or shaking. Alternatively, the application of ultrasound may be used as a means of agitation. Hyperpolarisation transfer by replacing the $H_2$ gas with p-$H_2$ may be performed to create a hyperpolarised transference complex whilst agitating the system as described herein.

The addition of $H_2$ or parahydrogen (p-$H_2$) gas to the solvent may take place prior to the solvent system being agitated or may take place concurrent with agitation. Catalyst activation under parahydrogen may take place prior to the final hyperpolarisation transfer step or be part of the hyperpolarisation transfer step.

The magnetisation transfer complex substrate and the recipient metal complex may each contain appropriate $^2$H or Cl or O labels to maximise the relaxation times of the nuclear spins that are to be hyperpolarised (e.g. $^1$H, $^{13}$C, $^{31}$P, $^{15}$N, $^{29}$Si or $^{19}$F). The substrate may contain appropriate $^{13}$C or $^{15}$N labelling to maximise the proportion of the substrate that can be created in a hyperpolarised NMR visible form in conjunction with appropriate $^2$H, O or Cl labelling to extend their magnetic state lifetimes. Thus, the selected small molecule transference substrate may contain spin pairs of appropriate $^1$H, $^{13}$C, $^{31}$P, $^{15}$N, $^{29}$Si or $^{19}$F labels to enable the formation of long-lived states (singlet states) between the corresponding spin pairs (e.g. $^1$H, $^{13}$C, $^{31}$P, $^{15}$N, $^{29}$Si or $^{19}$F) within a molecular scaffold that contains appropriate $^2$H or Cl labelling to extend their lifetime. Long lived states may be created from a variety of spin pairs, including pairs comprising $^1$H, $^{13}$C, $^{15}$N, $^{31}$P, $^{29}$Si and $^{19}$F nuclei. The small molecule transference substrate will generally contain its spin ½ nuclei (e.g. $^1$H, $^{13}$C, $^{31}$P, $^{15}$N, $^{29}$Si or $^{19}$F) at the natural abundance level. In the case where the small molecule transference substrate contains pairs, these may be homo-nuclear or hetero-nuclear in nature. Examples, of such pairs include, but shall not be limited to $^1$H/$^1$H, $^1$H/$^{13}$C, $^1$H/$^{19}$F, $^1$H/$^{15}$N or $^{13}$C/$^{13}$C or any other combination of spin one half nuclei.

Hyperpolarisation will be transferred from parahydrogen into the small molecule transference substrate in an optimised magnetic field to create a strongly hyperpolarised response that is subsequently converted into a singlet state across the spin-pair. This conversion may occur spontaneously or may be promoted by radio frequency excitation.

The type of magnetic states required in this process may be ultra-low magnetic fields, e.g. <1G (<$10^{-4}$T) which can spontaneously hyperpolarise the said singlet state.

A magnetisation transfer complex will generally comprise a magnetisation transfer catalyst provided with at least one suitable ligation site enabling it to interact with one or more small molecule transference substrates. Preferably, the magnetisation transfer catalyst may comprise two ligation sites, e.g. for two substrate molecules. When two ligation sites are present the two substrate molecules may be positioned trans to the two ligation sites, e.g. for para-$H_2$ derived hydrides.

A magnetisation transfer catalyst which shall include, but shall not be limited to, iridium based catalysts.

Preferred (SABRE) hyperpolarization transfer catalysts are thus described in our co-pending application No. PCT/GB2009/002860. Such catalysts include, for example, [IrCl(COD)IMes] and analogues thereof, (in which COD is cycloocta-1,5-diene). Alternatively, the (SABRE) hyperpolarization transfer catalyst may comprise a $^2$H-labelled counterpart of [IrCl(COD)IMes] or a catalyst optimised to work in the non-aqueous phase with the selected substrate.

Generally, an iridium magnetisation transfer catalyst will include iridium with at least one N-heterocyclic carbene (NHC) ligand.

Examples of such N-heterocyclic carbenes include, but shall not be limited to:

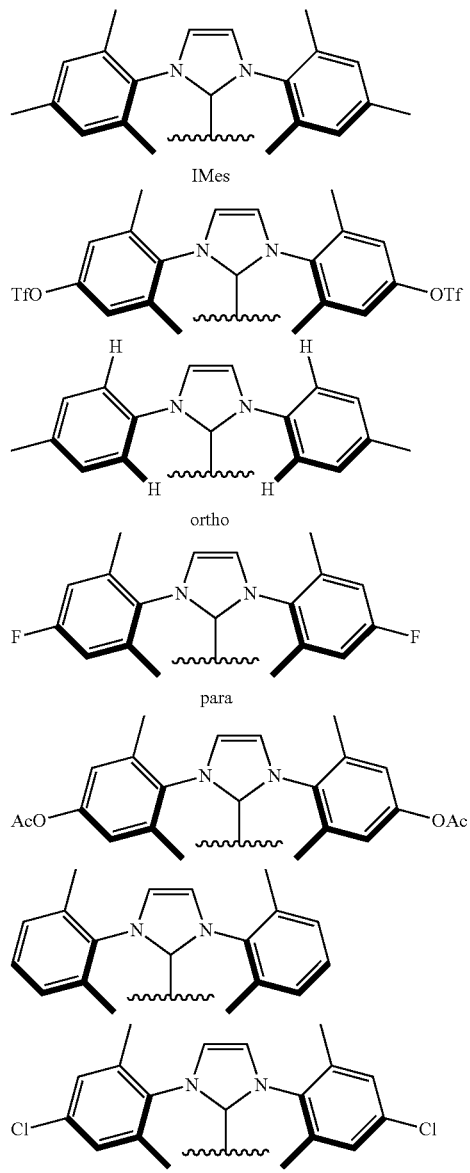

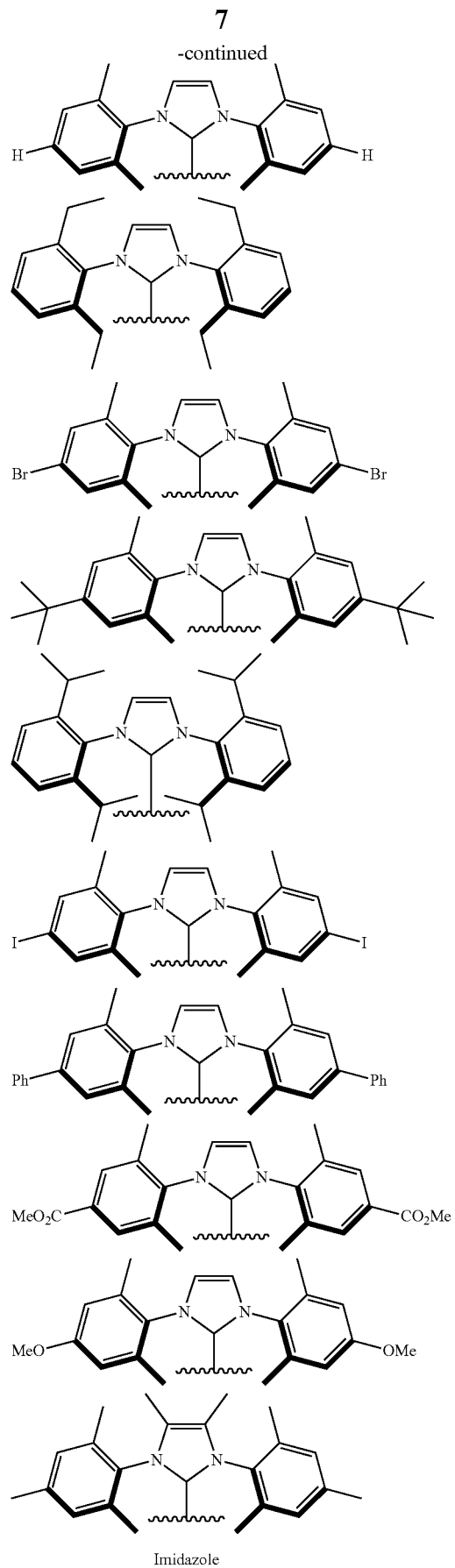
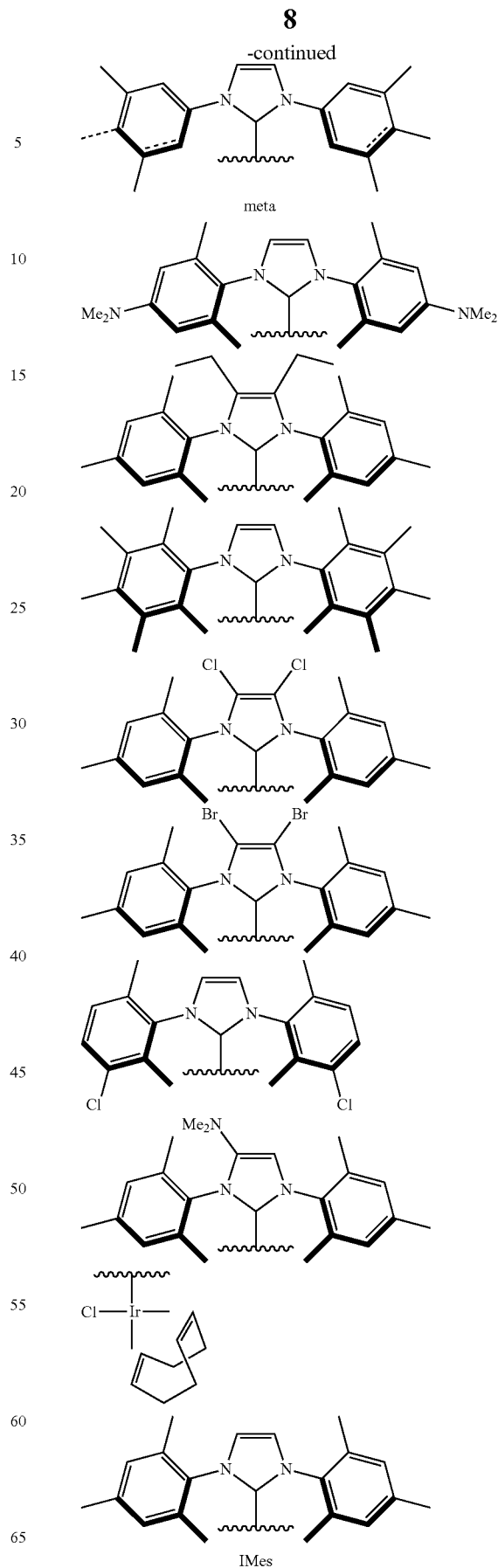

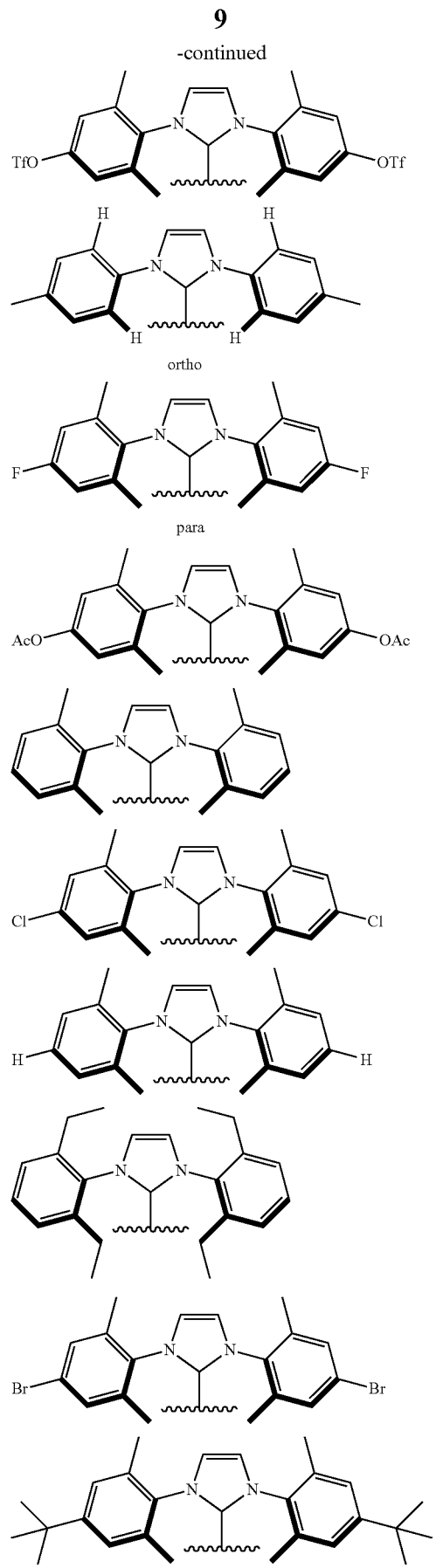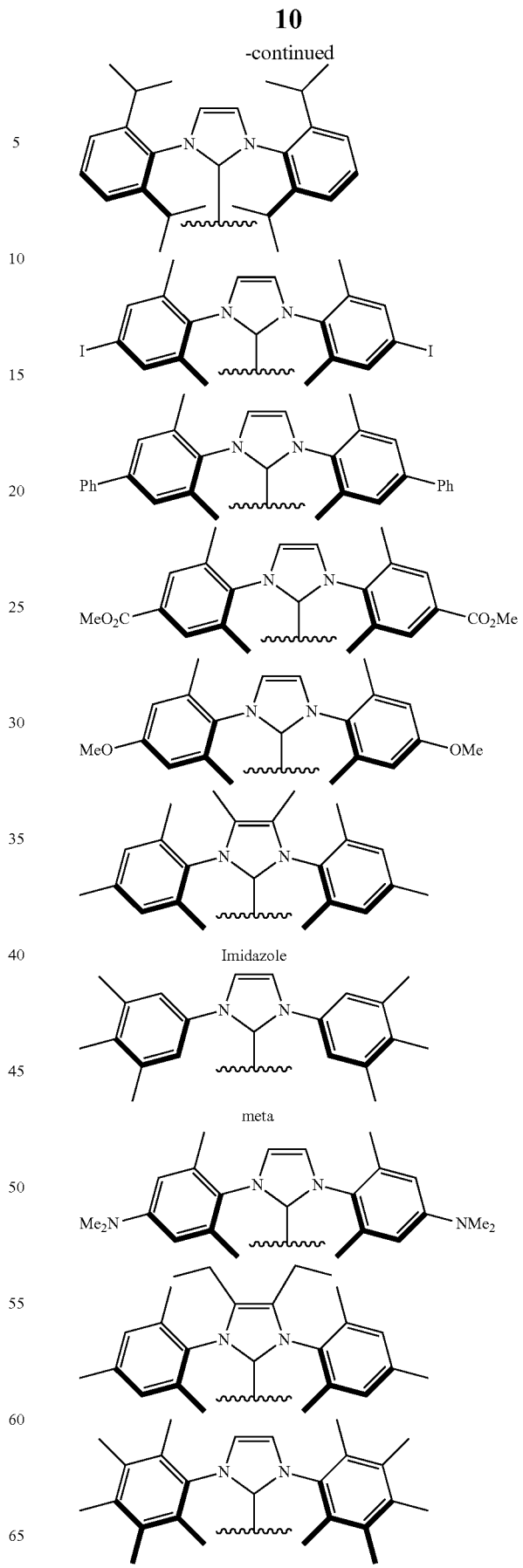

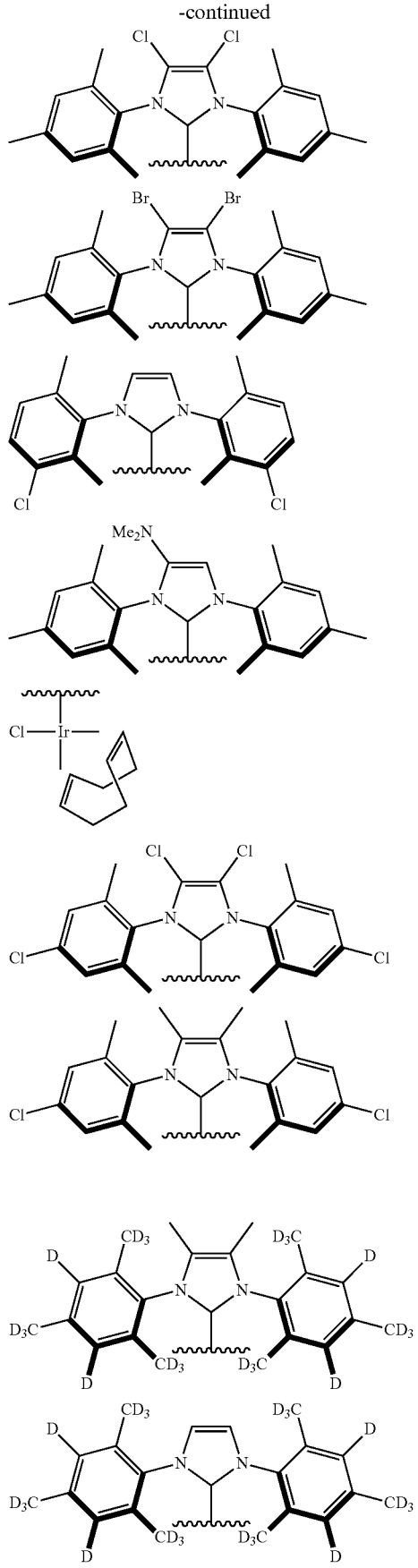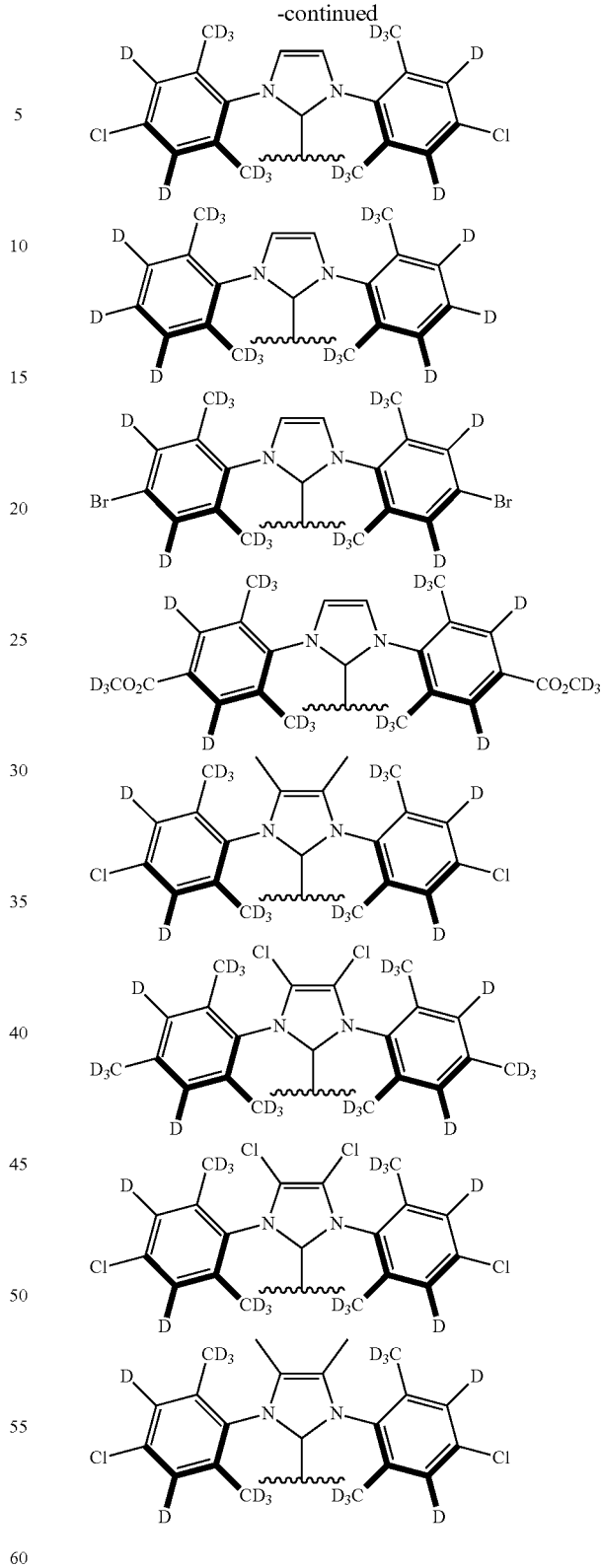

These species are often referred to as precatalysts because they are stable and become active during the catalytic process, in this case through their reaction with the small molecule transference substrate and $H_2$ The small molecule transference substrate will generally comprise at least one suitable ligation site (e.g. N, S, C or O) to interact with the initial magnetisation transfer catalyst.

Examples of hyperpolarised transference substrates include, but shall not be limited to, pyridine (py), pyridazine (pdz), methyl-pyridazine (methyl-pdz), $d_2$-nicotinate (nic) and $Cl_2$-$d_2$-$^{15}N_2$-pyridazine. For the avoidance of doubt, the small molecule transference substrate does not comprise either diphenylacetylene or diethyl oxalate.

In one aspect of the invention the recipient complex is a recipient metal complex. The recipient metal complex is able to harness the properties of the newly hyperpolarised small molecule transference substrate that exists in a singlet nuclear state, to sensitise the detection of a second substrate, e.g. the recipient substrate.

In a second form of this process, the recipient metal complex and the recipient substrate may be present at point (i), i.e. when the recipient metal complex bound to the small molecule transference substrate is hyperpolarised.

In a further aspect of the present invention a biphasic element may be introduced in order to enable the hyperpolarisation transfer process to be completed in a single vessel. This may involve preparing a fluid containing two separate components, where one is in water and the second an immiscible co-solvent (e.g. An organic solvent, such as, toluene, chloroform or dichloromethane). Where the ratio of phases is selected to maximise the degree of recipient hyperpolarization and/or to maximise the speed of phase separation.

When required, the aqueous solvent mixture combination may be used to maximise the relaxation time of the hyperpolarised recipient complex in this solution by:
 (i) employing $D_2O$;
 (ii) employing a $D_2O$ $H_2O$ mixture of suitable proportion e.g. 1:1; or
 (iii) adding a further co-solvent to an appropriate aqueous phase, such as, ethanol or $d_6$-ethanol.

One or more solvent phase-separation promoter(s), e.g. NaCl or $NaO_2CCH_3$ or NaOH or $NaHCO_3$ or $Na_2CO_3$ or ethanol may be added at a suitable concentration:
 (i) to achieve suitable physiological conditions;
 (ii) to vary the pH of the solution in order to achieve optimal SABRE;
 (iii) to optimise an organic phase extraction; and/or
 (iv) to optimise the speed of phase-separation.

In the method of the invention an appropriate amount of time may be allowed to permit the phase separation to occur.

The result of the process is that the hyperpolarised singlet state population of the small molecule transference substrate is utilised to hyperpolarise the nuclear spins of a second material. In order for this to happen the hyperpolarised small molecule transference substrate and the second material, the recipient substrate, are each capable of binding reversibly to the second complex, the recipient complex. This process will take place in a magnetic field that allows the optimal transfer of hyperpolarisation into the second material, the recipient substrate.

The recipient metal complex will usually comprise a transition metal complex, for example comprising a metal atom selected from, but not limited to, Ru, Rh, Ir, W, Pd and Pt. The complex will usually comprise one or more ligands in addition to the ligand comprising the hyperpolarisable nuclei. These one or more other ligands may comprise organic or inorganic ligands and may be mono-, bi- or multidentate in nature. These one or more ligands may play a role in controlling the activity and stability of the metal centre. For example, the one or more ligands may comprise NHC ligands as herein described.

In one embodiment, the metal complex comprises one or more phosphine ligands in addition to the ligand to be hyperpolarized. The metal complex may be attached to a solid support, for example a polymer support. Attachment will usually be made through a ligand which links the metal centre to the support. Suitable linkers are known in the art. For example, the linker may comprise one or more in-chain atoms selected from C, P, N, S, P and Si. The linker may comprise a siloxane moiety for attachment to the support and/or a phosphine moiety for attachment to the metal of the complex. In embodiments, the linker is a group of the following formula: —O—Si(OMe)$_2$—(CH$_2$)$_n$—P(Cy)$_2$—, wherein n is 0 upwards (e.g. 0, 1, 2, 3, 4, 5 or 6) and Cy is cyclohexyl.

The recipient metal complex will contain appropriate $^{13}$C or $^{15}$N labelling to maximise the proportion of the complex that can be created in a hyperpolarised NMR visible form in conjunction with appropriate $^2$H or Cl labelling to extend their magnetic state lifetimes.

The recipient metal complex will contain pairs of appropriate $^1$H, $^{13}$C, $^{31}$P, $^{15}$N or $^{19}$F labels to enable the formation of long-lived states (singlet states) between the corresponding spin pairs (e.g. $^1$H, $^{13}$C, $^{31}$P, $^{15}$N, $^{29}$Si or $^{19}$F) within a molecular scaffold that contains appropriate $^2$H or Cl labelling to extend their lifetime.

The recipient substrate will contain a ligating group such as O, N, S, P, or C to enable binding to the second metal complex. Suitable substrates include, but shall not be limited to compounds like nicotinamide, nicotine, pyrazine, 5-methyl pyrimidine, acetate, pyruvate, ethoxide, hydroxide, oxalate or gluconate, sugars like glucose or fructose, urea, amides, amino acids like glutamate, glycine, cysteine or aspartate, GABA (γ-aminobutyric acid), nucleotides, vitamins like ascorbic acid, serotonin, penicillin derivatives and sulphonamides; or salts of these agents, where such salts exist. It is further stated that intermediates in normal metabolic cycles such as the citric acid cycle like fumaric acid and pyruvic acid may suitably be utilised as a recipient substrate, since they are suitable imaging agents for the imaging of metabolic activity.

The recipient complex is designed to produce an optimal lifetime and coupling framework for hyperpolarisation transfer under these conditions. Given the different ligating properties on the two complexes, the transference complex and the recipient complex, it is possible through rational design to harness the properties of the recipient complex to bind the transference substrate, thereby harnessing the hyperpolarised singlet. Furthermore, the metal in the recipient complex, e.g. Ru, Rh, Ir, W, Pd and Pt, may already contain the recipient substrate or through ligand exchange either bind the recipient substrate through a ligating centre such as oxygen. In this way a range of substrate classes can be optimally hyperpolarised thereby overcoming one of the major limitations of the existing parahydrogen based technologies.

In a further variant the recipient complex may contain a slow or non-dissociating pair of binding sites such as $^{31}$P which can receive the singlet state after transfer from the transference substrate. Loss of the transference substrate and binding of the recipient substrate will then enable its hyperpolarisation which returns to the bulk solution after dissociation.

In a yet further variant of this approach, the recipient metal complex may be replaced by a molecular agent with a three dimensional structure such as a protein, enzyme, polysaccharide, DNA or RNA and interaction with this molecular organised motif will break the symmetry of the singlet state in order to enable hyperpolarisation transfer into the molecular agent. In this way the molecular agent will become sensitised to NMR or MRI detection. This approach is therefore suited to the characterisation of large molecules and the probing of drug binding, active site conformations and dynamics and folding. Therefore, for the avoidance of doubt, the recipient complex shall be construed as encompassing a three dimensional structure, such as, a protein, enzyme, polysaccharide, DNA and RNA.

In a further aspect of the present invention hydrogen bonding may be utilized to facilitate short-term molecular interaction for between the transference substrate and the recipient complex. Alternatively, bisulfide linkages may be utilised to establish a short-term interaction. In a further alternative, ionic interactions may be utilized to produce the required short-term molecular order. In a yet further alternative, Van der Waals forces may be utilised to produce the required short-term molecular order required for hyperpolarisation transfer.

The interactions detailed above may be harnessed to probe specific aspects of structure by introducing a molecular recognition element. For example, if a protein is being examined then amino acid residues, such as, tyrosine, threonine or glutamic acid residues, might be specifically selected. Given that DNA binding relies on a series of matches, adding a 3-mer DNA strand would enable specific backbone sequences to be readily identified.

For in vivo use an in-line UV probe may be used, if desired, to establish that the magnetisation transfer complex concentration is sufficiently low for in vivo injection. This makes full use of the fact that the catalyst is no longer present and therefore unable to promote the relaxation of the agent in an aqueous phase, thereby maximising longevity of the resulting hyperpolarised signal.

For systems where the catalyst concentration remains too high in the aqueous phase, a catalyst deactivator may be added, to facilitate catalyst transfer to the non-aqueous phase. Example of a suitable catalyst deactivators include, but shall not be limited to, bipyridyl, EDTA and dimethylglyoxime.

An appropriate delivery device may be used to procure the recipient complex for detection by NMR or MRI which can facilitate some or all of the following:
  (i) after an appropriate amount removing a hyperpolarised sample from an aqueous phase;
  (ii) using UV monitoring to assess suitability immediately prior to sample removal or after sample removal;
  (iii) using pH monitoring to immediately assess suitability prior to sample removal or after sample removal;
  (iv) employing filtration to achieve sterility after sample removal;
  (v) injecting or transporting the sample into a target for subsequent detection by NMR or MRI, where the target might be a suitable sample tube, an animal or a human.

According to a further aspect of the invention there is provided a method of producing a hyperpolarised target substrate imaging medium, said method comprising the steps of:
  (i) preparing a system containing a magnetisation transfer complex, said complex including a reversibly bound small molecule transference substrate;
  (ii) adding $H_2$ or parahydrogen ($p$-$H_2$) gas to the system;
  (iii) applying a magnetic field such that hyperpolarisation is transferred into the transfer complex, including the reversibly bound small molecule transference substrate;
  (iv) separately or simultaneously introducing a recipient complex capable of binding the small molecule transference substrate, said recipient complex including a recipient substrate, such that the recipient complex and recipient substrate, including the bound transference substrate, is hyperpolarised; and
  (v) separating the hyperpolarised recipient complex; the hyperpolarised recipient substrate; or the transference substrate to provide a hyperpolarised target substrate imaging medium.

According to a further aspect of the invention there is provided a pharmaceutically acceptable formulation comprising a solution of a hyperpolarised recipient substrate for use as an imaging medium, wherein said hyperpolarised recipient substrate is prepared by transfer from a hyperpolarised singlet state that is not parahydrogen, said method comprising the steps of:
  (i) preparing a system containing:
    parahydrogen; a magnetisation transfer complex, with a molecular symmetry that allows the creation of a singlet state between spin pairs within it, said complex including a reversibly bound small molecule transference substrate;
    applying a magnetic field such that hyperpolarisation is transferred into the transfer complex, including the reversibly bound small molecule transference substrate;
  (ii) separately or simultaneously introducing a recipient complex capable of binding the small molecule transference substrate, said recipient complex including a recipient substrate, such that the recipient complex and recipient substrate, including the bound transference substrate, are hyperpolarised.

Suitable substrates include, but shall not be limited to compounds like nicotinamide, nicotine, pyrazine, 5-methyl pyrimidine, acetate, pyruvate, ethoxide, hydroxide, oxalate or gluconate, sugars like glucose or fructose, urea, amides, amino acids like glutamate, glycine, cysteine or aspartate, GABA (γ-aminobutyric acid), nucleotides, vitamins like ascorbic acid, serotonin, penicillin derivatives and sulfonamides. In a particular aspect of the present invention the recipient substrate is pyruvate. It is further stated that intermediates in normal metabolic cycles such as the citric acid cycle like fumaric acid and pyruvic acid may suitably be utilised a recipient substrate, since they are suitable imaging agents for the imaging of metabolic activity.

In a preferred aspect of the invention the pharmaceutically acceptable formulation comprises a solution of a hyperpolarised recipient substrate in a saline solution of a hyperpolarised substrate for use as an imaging medium.

According to a yet further aspect of the invention there is provided an imaging medium for in vivo magnetic resonance (MR) detection comprising a hyperpolarised recipient substrate wherein said hyperpolarised recipient substrate is prepared by transfer from a hyperpolarised singlet state that is not parahydrogen, said method comprising the steps of:
  (i) preparing a system containing:
    parahydrogen; a magnetisation transfer complex, with a molecular symmetry that allows the creation of a singlet state between spin pairs within it, said complex including a reversibly bound small molecule transference substrate;
    applying a magnetic field such that hyperpolarisation is transferred into the transfer complex, including the reversibly bound small molecule transference substrate;
  (ii) separately or simultaneously introducing a recipient complex capable of binding the small molecule transference substrate, said recipient complex including a recipient substrate, such that the recipient complex and recipient substrate, including the bound transference substrate, are hyperpolarised.

The invention will now be illustrated by way of example only and with reference to the accompanying drawings, in which.

Figure 10:
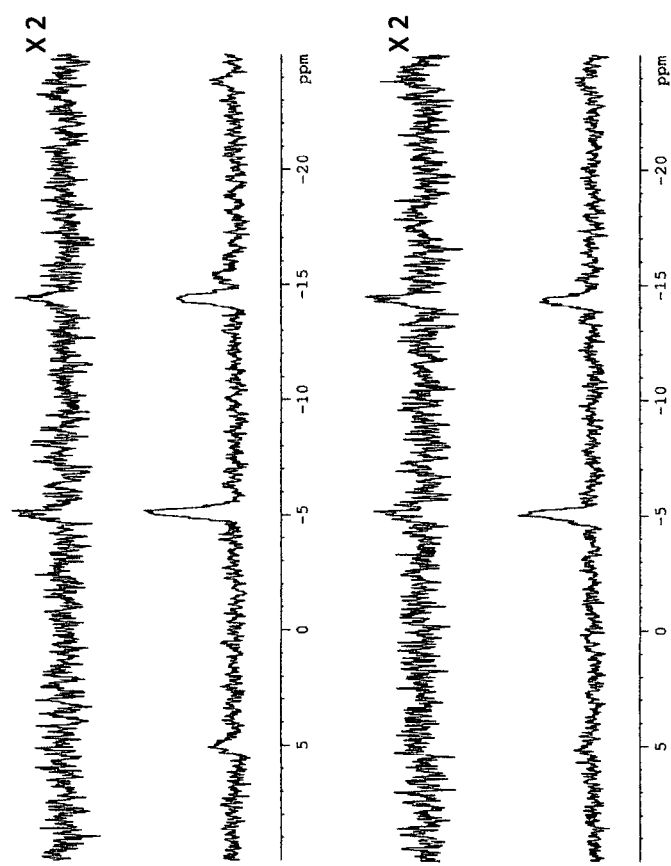
Figure 11:
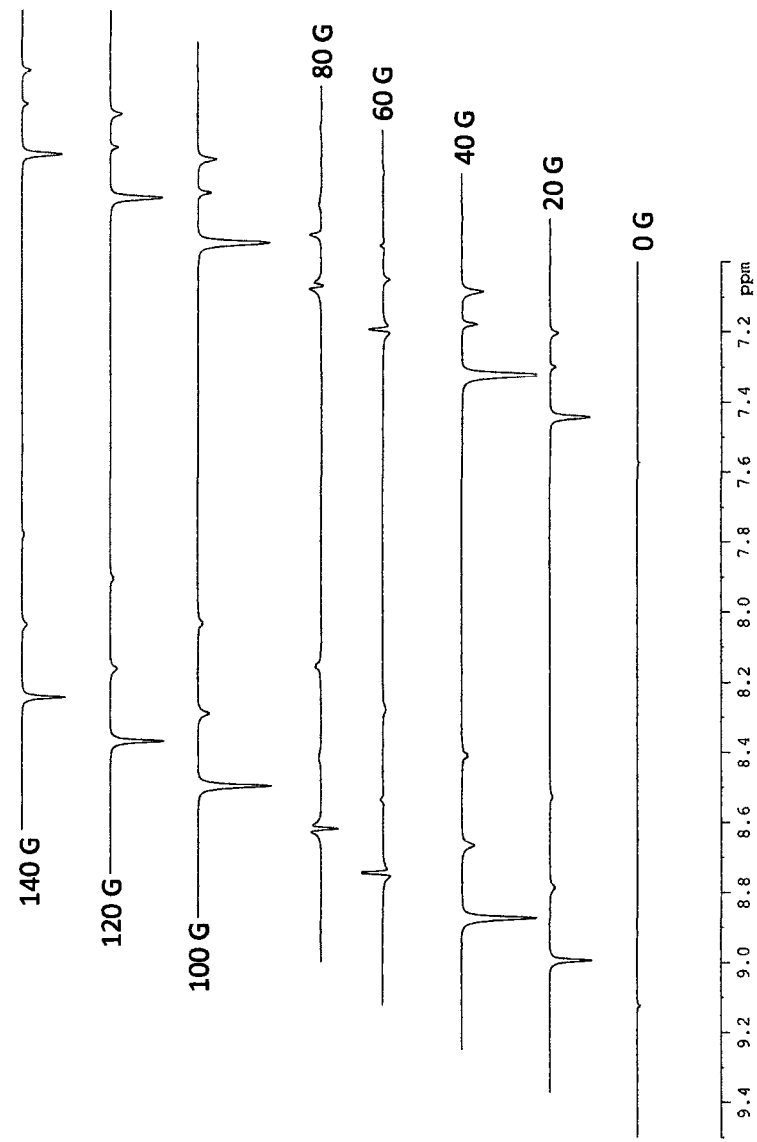
Figure 12:
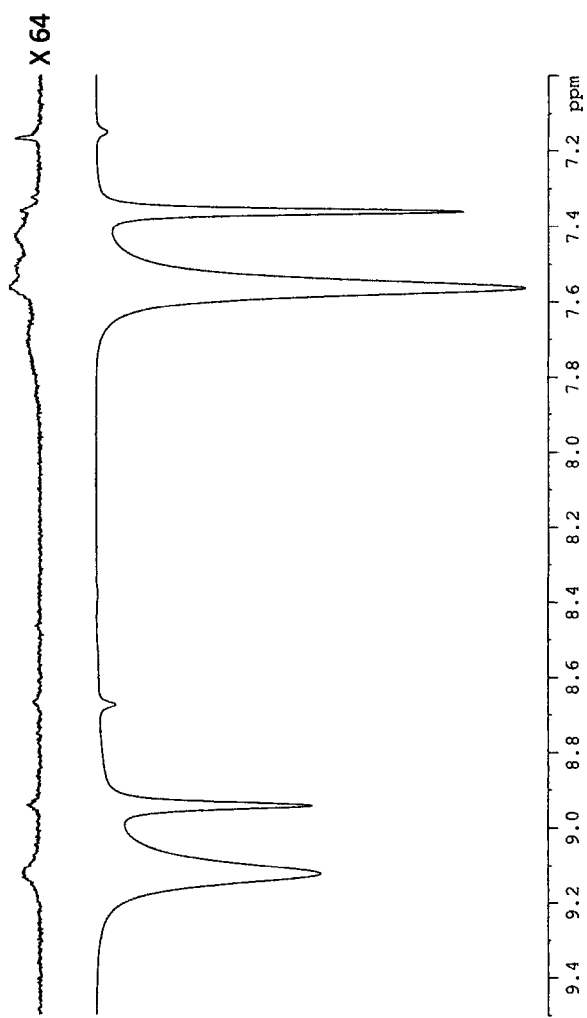
Figure 13:
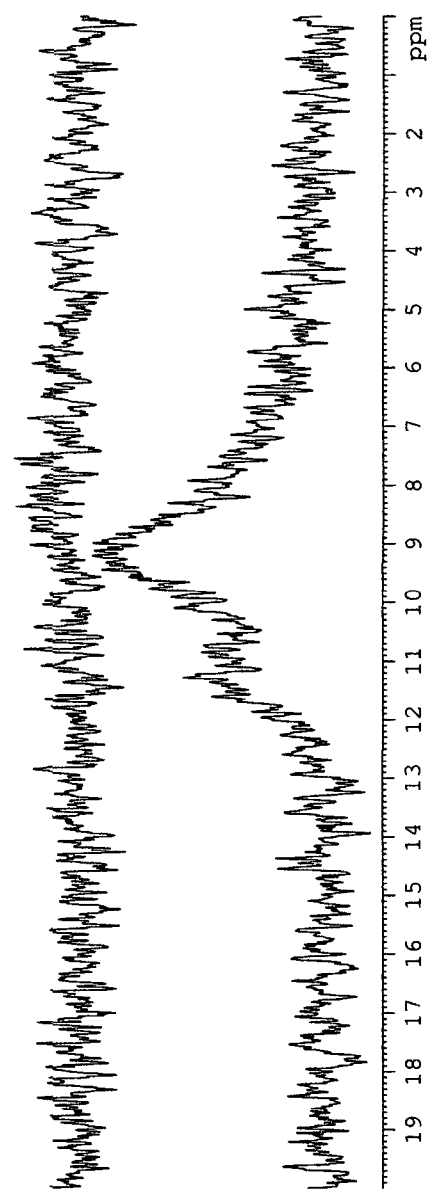
Figure 14:
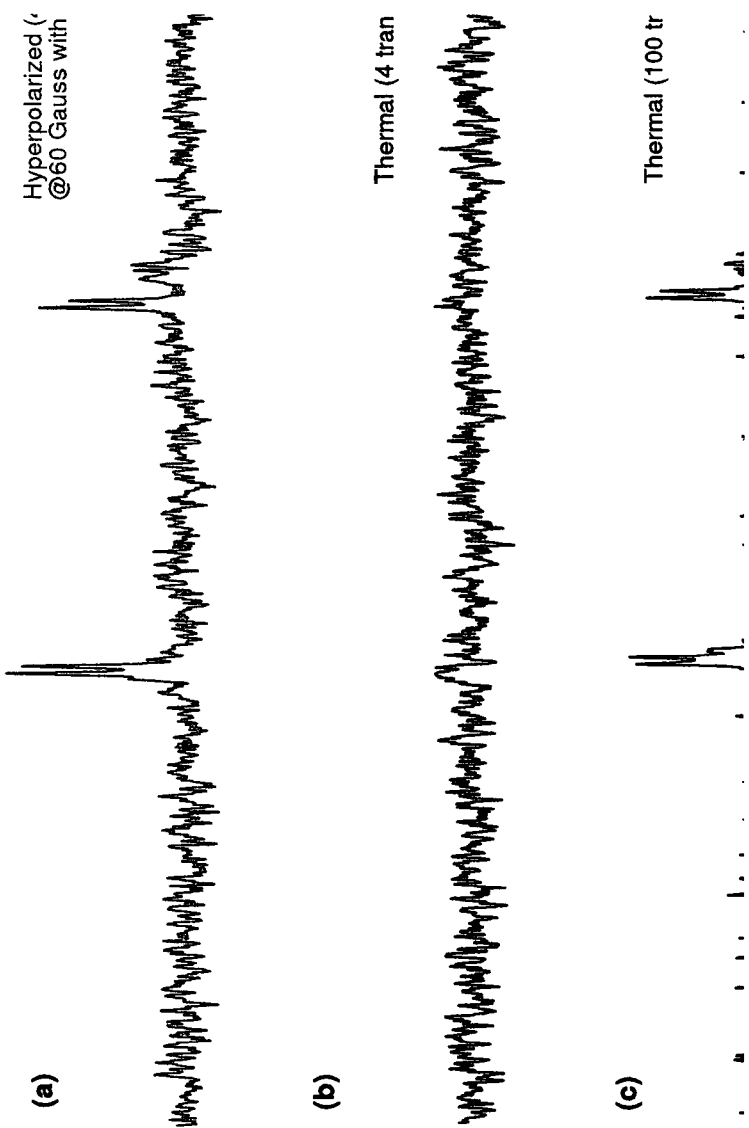

FIG. 10 is a comparison of the 4-scan $^{31}$P NMR spectra collected under Boltzmann conditions (above, with signal multiplied by 2 in both cases), and the 4-scan $^{31}$P NMR spectra collected under SABRE conditions of a d$_4$-methanol solution containing [IrCl(COD)(IMes)], [Pt(OTf)$_2$(dppp)] and d$_2$-nicotinate (the top set of NMR spectra were collected using a 90° pulse, whereas the bottom set were collected using a 45° pulse);

FIG. 11 is a comparison of the $^1$H NMR spectra collected under SABRE conditions of a d$_4$-methanol solution containing [IrCl(COD)(IMes)], [Pt(OTf)$_2$(dppp)] and d$_2$-nicotinate at different polarisation transfer fields;

FIG. 12 is a comparison of the $^1$H NMR spectrum collected under Boltzmann conditions (above, with signal multiplied by 64), and the $^1$H NMR spectrum collected under SABRE conditions of a d$_4$-methanol solution containing [IrCl(COD)(IMes)], [Pd(OTf)$_2$(dppp)] and d$_2$-nicotinate;

FIG. 13 is a comparison of the 45° pulse 4-scan $^{31}$P NMR spectra collected under Boltzmann conditions (above), and the 45° pulse 4-scan $^{31}$P NMR spectra collected under SABRE conditions of a d$_4$-methanol solution containing [IrCl(COD)(IMes)], [Pd(OTf)$_2$(dppp)] and d$_2$-nicotinate; and FIG. 14 illustrates (a) Hyperpolarized $^{31}$P$\{^1$H$\}$ NMR spectra of d2-nicotinate mixed with 2 variants of catalyst and dissolved in d$_4$-methanol solution. The spectra were acquired over 4 transients under optimized (60 G mixing field) SABRE conditions and using a double-quantum filter. Thermally acquired NMR spectra of the same solution in equilibrium when acquired over (b) 4 transients and (c) 100 transients. A net enhancement of ~25-fold are observed for $^{31}$P nuclei attached to [Pd(py)$_2$(dppp)] catalyst.

EXAMPLE 1

Metal Complex 1

The first complex investigated for these purposes is shown in Scheme 1. It is a platinum complex chelated by a bidentate 1,3-bis(diphenylphosphino)propane (dppp) ligand and two triflate ligands. The bis-chelating dppp acts to stabilise the platinum, whilst the triflate ligands are labile and easily displaced by N-heterocycles. Once they have been displaced, they act as anions and stabilise any positive platinum complexes that result.

Scheme 1 [Pt(OTf)$_2$(dppp)], proposed to exchange its triflates for polarised N-heterocycles.

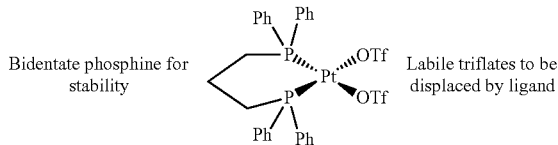

Bidentate phosphine for stability

Labile triflates to be displaced by ligand

[Pt(OTf)$_2$(dppp)] was synthesised according to the pathway shown in Scheme 2. Platinum dichloride was refluxed in neat benzonitrile to form [Pt(Cl)$_2$(PhCN)$_2$]. The benzonitrile was then displaced with dppp to form [Pt(Cl)$_2$(dppp)]. The chlorides were abstracted using silver triflate to form silver chloride, with the triflate ligands now binding to platinum, forming [Pt(OTf)$_2$(dppp)].

Scheme 2 Synthesis of [Pt(OTf)$_2$(dppp)].

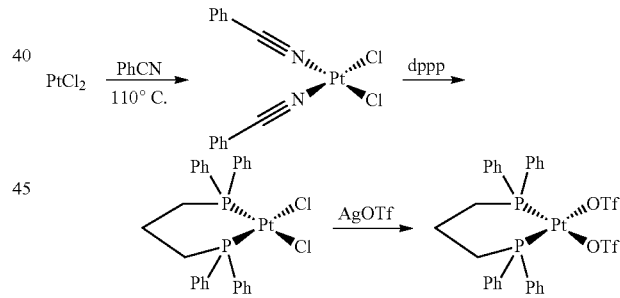

EXAMPLE 2

Metal Complex 1 with Pyridine

Figure 1:
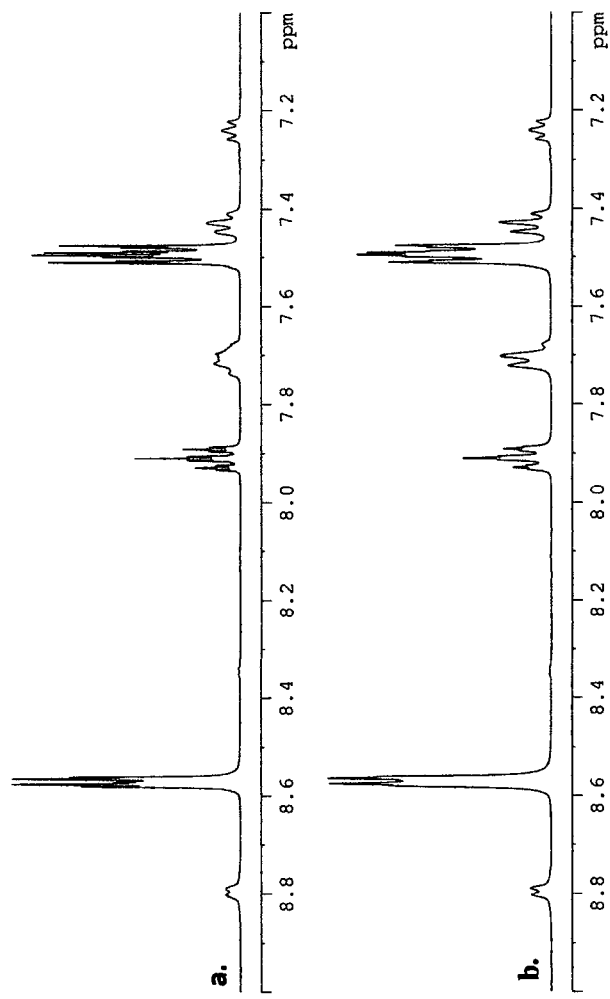
FIG. 1 is a $^1$H NMR spectrum (a.) and $^1$H $\{^{31}$P$\}$ NMR spectrum (b.) of [Pt(OTf)$_2$(dppp)] in d$_4$-methanol, with pyridine.
Figure 2:
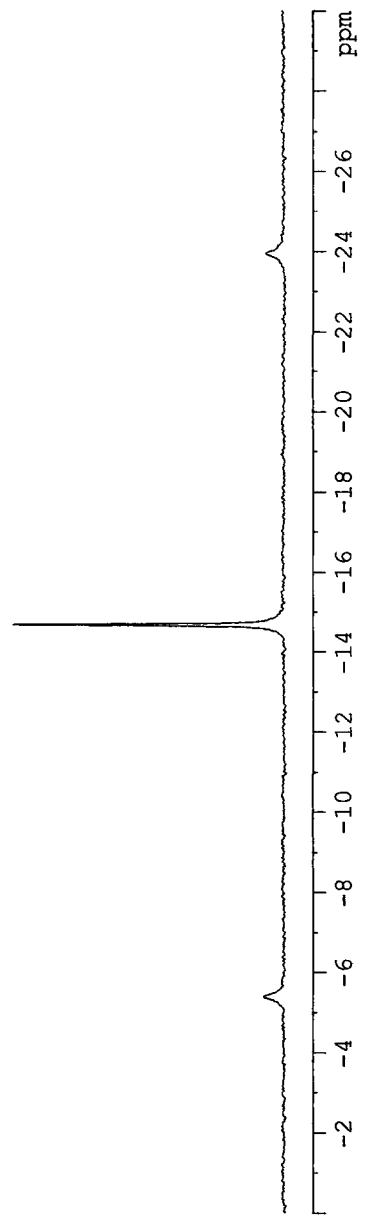
FIG. 2 is a $^{31}$P $\{^1$H$\}$ NMR spectrum of [Pt(OTf)$_2$(dppp)] in d$_4$-methanol, with pyridine.
Figure 3:
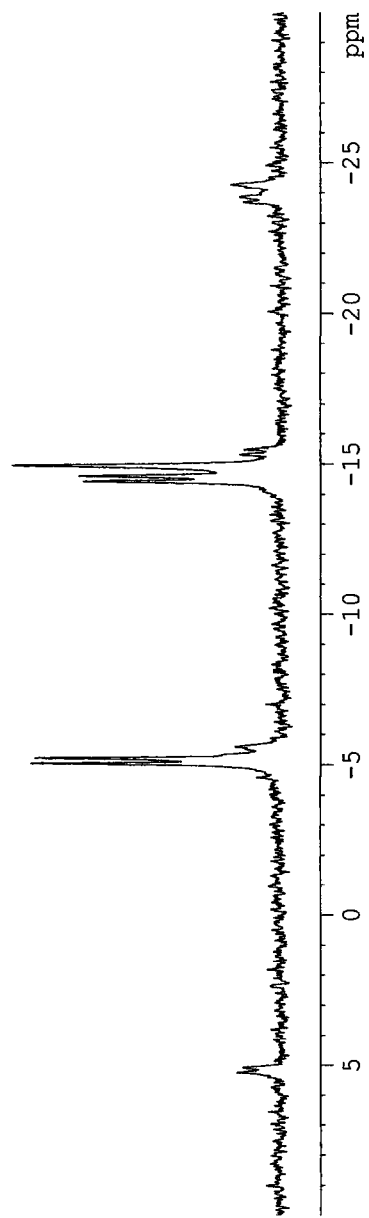
FIG. 3 is a $^{31}$P $\{^1$H$\}$ NMR spectrum of a d$_4$-methanol solution containing [IrCl(COD)(IMes)], [Pt(OTf)$_2$(dppp)] and pyridine.

Displacement of the triflate ligands of [Pt(OTf)$_2$(dppp)] in d$_4$-methanol with 10 equivalents of pyridine (py) was investigated. NMR spectra were collected to identify any signals corresponding to bound pyridine. The $^1$H and $^1$H $\{^{31}$P$\}$ NMR spectra are given in FIGS. 1 and 2.

In the $^1$H NMR spectrum the large signals at δ 8.57, 7.91 and 7.50 correspond to unbound pyridine in solution. The smaller signals at δ 8.80, 7.71, and 7.24, correspond to the ortho, para, and meta protons of pyridine bound to platinum and those at δ 7.72, 7.50 (hidden beneath unbound pyridine peak), and 7.43 correspond to the ortho, para, and meta protons of the phenyl rings in dppp.

The $^{31}$P {$^1$H} NMR spectrum contains just one singlet at δ −14.68 with a J$_{PPt}$ splitting of 3000 Hz. The singlet nature of the $^{31}$P NMR signal confirms that the platinum complex has C$_{2v}$ symmetry, which can only be the case when both triflate ligands are replaced with pyridine, forming [Pt(py)$_2$(dppp)][OTf]$_2$, shown in Scheme 3.

Scheme 3 [Pt(py)$_2$(dppp)][OTf]$_2$.

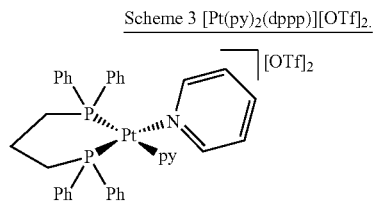

This evidence supports the potential for [Pt(OTf)$_2$(dppp)] to bind to polarised N-heterocycles which may transfer polarisation to the ligands at platinum.

EXAMPLE 3

Metal Complex 1 with pyridine and [IrCl(COD)(IMes)]

Scheme 4 Transfer of polarised ligand between iridium and platinum (charges not shown).

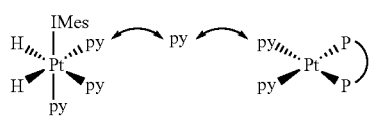

Exchange of hyperpolarised pyridine ligands of [Ir(H)$_2$(IMes)(py)$_3$]Cl with [Pt(py)$_2$(dppp)] in d$_4$-methanol with 10 equivalents of pyridine (py) was investigated. NMR spectra were first collected to identify any different platinum complexes that formed in the presence of [IrCl(COD)(IMes)] signals. There were no obvious differences in the $^{31}$P {$^1$H} NMR spectrum collected with [IrCl(COD)(IMes)] present, therefore the same [Pt(py)$_2$(dppp)] complex was present in solution.

Figure 4:
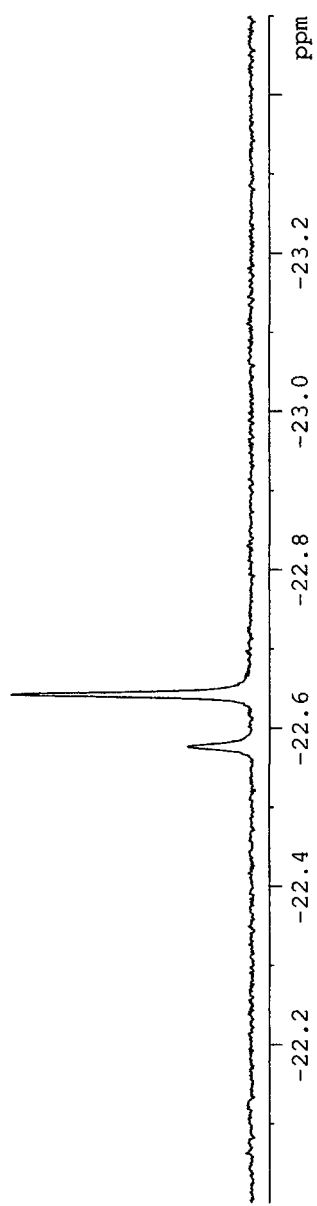
FIG. 4 is a $^1$H NMR spectrum of the signals observed in the hydride region of a d$_4$-methanol solution containing [IrCl(COD)(IMes)], [Pt(OTf)$_2$(dppp)] and pyridine.

On 'activation' of the iridium complex with para-H$_2$, the $^{31}$P {$^1$H} NMR spectrum changed due to the formation of a new platinum complex. In addition to the original singlet observed at δ −14.68, two doublets were also observed at δ −5.09 and −14.49, each with J$_{PP}$=28.1 Hz. These likely correspond to the platinum complex given in Scheme 5, where now only one pyridine molecule is bound to platinum. The characteristic signals for the active iridium complex, shown in Scheme 4, were also observed and the corresponding hydride is shown in FIG. 4 (δ −22.64). A second hydride is also present at δ −22.58, which is likely to correspond to the hydride ligand in the same complex, but where one hydride ligand is now replaced with deuterium.

Scheme 5 [Pt(OTf)(py)(dppp)].

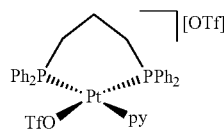

Figure 5:
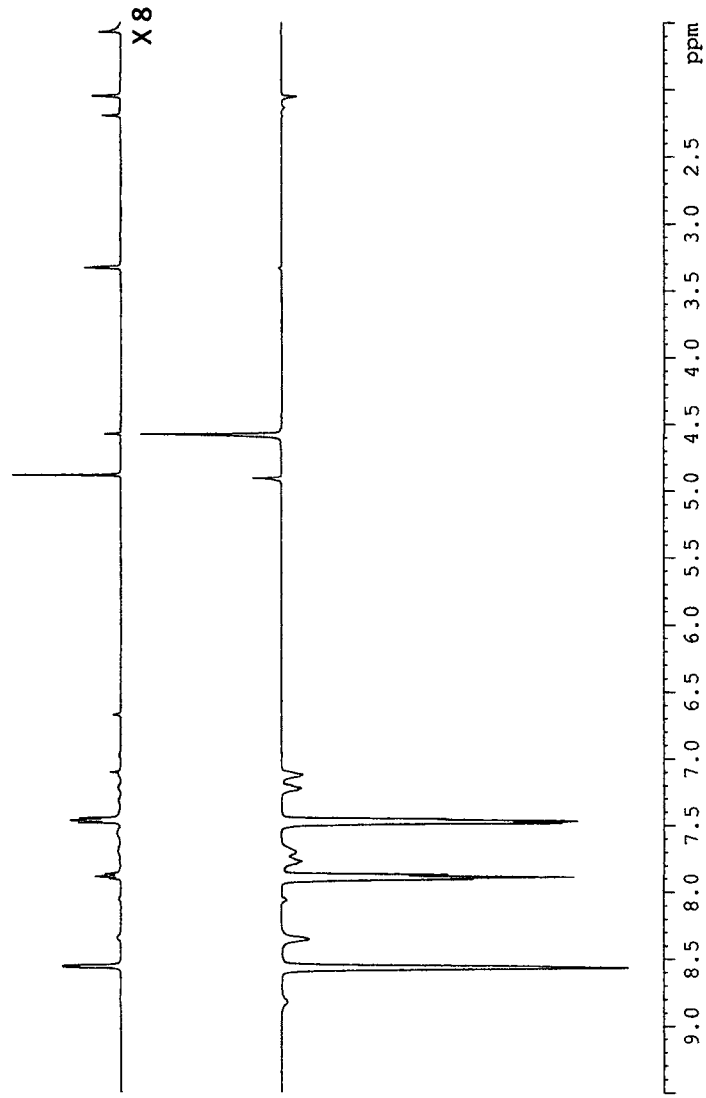
FIG. 5 is a comparison of the $^1$H NMR spectrum collected under Boltzmann conditions (above, with signal multiplied by 8), and the $^1$H NMR spectrum collected under SABRE conditions of a d$_4$-methanol solution containing [IrCl(COD)(IMes)], [Pt(OTf)$_2$(dppp)] and pyridine.

Replacing the hydrogen gas in the sample with para-H$_2$ (3 bar) led to the enhancement of all the signals in the aromatic region, thus the platinum complexes in solution must be hyperpolarised. An example spectrum is shown in FIG. 5.

Unfortunately, no polarisation transfer into the $^{31}$P nuclei was observed.

EXAMPLE 4

Metal Complex 1 with Pyridazine and [IrCl(COD)(IMes)]

Figure 6:
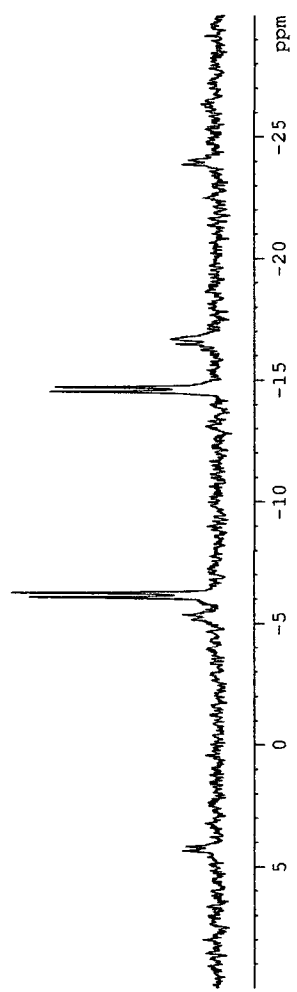
FIG. 6 is a $^{31}$P $\{^1$H$\}$ NMR spectrum of a d$_4$-methanol solution containing [IrCl(COD)(IMes)], [Pt(OTf)$_2$(dppp)] and pyridazine.

Exchange of hyperpolarised pyridazine ligands of [Ir(H)$_2$(IMes)(pdz)$_3$]Cl with [Pt(py)$_2$(dppp)] in d$_4$-methanol with 10 equivalents of pyridazine (pdz) was also investigated due to an increasing interest in the formation of singlet states on similar pyridazine ligands. NMR spectra were first collected to identify any different platinum complexes that formed in the presence of [IrCl(COD)(IMes)] and pyridazine. Although the $^1$H NMR spectra are more complicated, due to breaking of the C$_2$, symmetry of pyridazine on ligation of one nitrogen atom, the $^{31}$P {$^1$H} NMR spectrum (FIG. 6) confirm that a single platinum complex has formed, that contains two chemically inequivalent phosphorus nuclei. This is likely to be the complex given in Scheme 6, which is the pyridazine analogue of the pyridine complex mentioned previously.

Scheme 6 [Pt(OTf)(pdz)(dppp)][OTf]

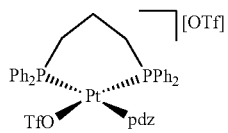

Figure 7:
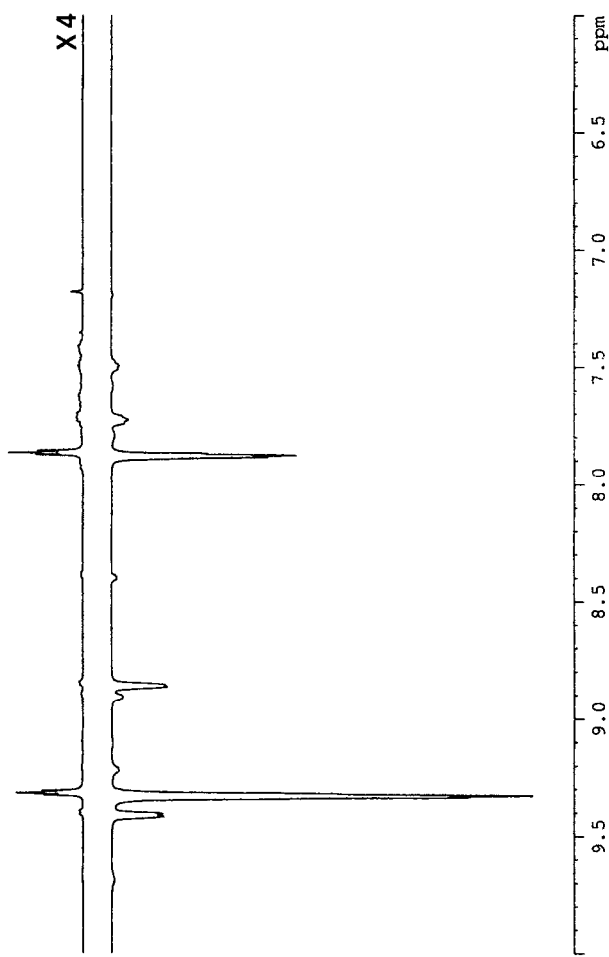
FIG. 7 is a comparison of the $^1$H NMR spectrum collected under Boltzmann conditions (above, with signal multiplied by 4), and the $^1$H NMR spectrum collected under SABRE conditions of a d$_4$-methanol solution containing [IrCl(COD)(IMes)], [Pt(OTf)$_2$(dppp)] and pyridazine.

Addition of para-H$_2$ resulted in the formation of [Ir(H)$_2$(IMes)(pdz)$_3$]Cl, which was identified by its characteristic $^1$H NMR hydride signal at δ−21.35. As with pyridine, polarisation transferred into all the aromatic signals corresponding to bound and free pyridazine (FIG. 7), which suggests that the bound pyridazine protons of [Pt(OTf)(pdz)(dppp)][OTf] are enhanced using this method.

Unfortunately, polarisation transfer to the $^{31}$P nuclei of [Pt(OTf)(pdz)(dppp)][OTf] was not observed by $^{31}$P {$^1$H} NMR.

EXAMPLE 5

Metal Complex 1 with d$_2$-nicotinate and [IrCl(COD)(IMes)]

Transfer of polarisation from d$_2$-nicotinate (Scheme7) onto the platinum complex was investigated. Deuterated nicotinate is already known to polarise effectively when using [IrCl(COD)(IMes)] and the polarised protons have long T$_1$ values, which makes this N-heterocycle a promising candidate for polarisation transfer to the platinum complex.

Scheme 7 d$_2$-dicotinate

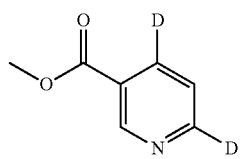

Figure 8:
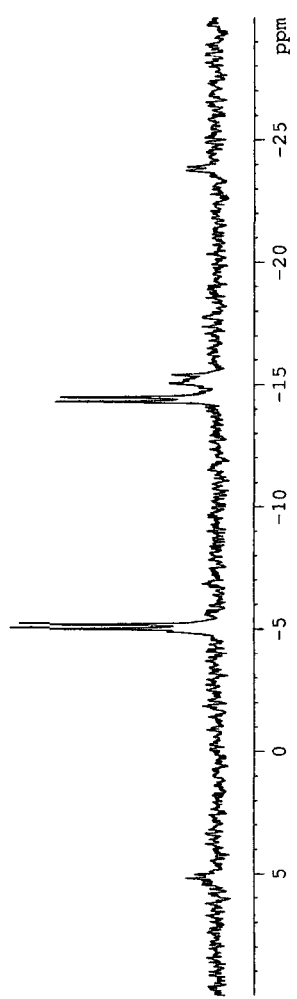
FIG. 8 is a $^{31}$P $\{^1$H$\}$ NMR spectrum of a d$_4$-methanol solution containing [IrCl(COD)(IMes)], [Pt(OTf)$_2$(dppp)] and d$_2$-nicotinate.

[IrCl(COD)(IMes)] and [Pt(py)$_2$(dppp)] were dissolved in d$_4$-methanol with 10 equivalents of d$_2$-nicotinate. NMR spectra were collected prior to the addition of para-H$_2$. As with the analogous pyridazine solution, only one platinum complex is present with two chemically inequivalent phosphorus nuclei (see FIG. 8). This likely corresponds to [Pt(OTf)(dppp)(nic)]OTf, shown in Scheme, where nic is d$_2$-nicotinate.

Scheme 8 [Pt(OTf)(dppp)(nic)]OTf

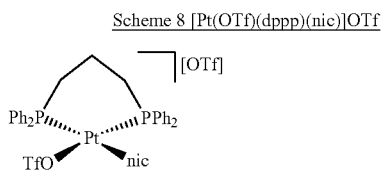

Figure 9:
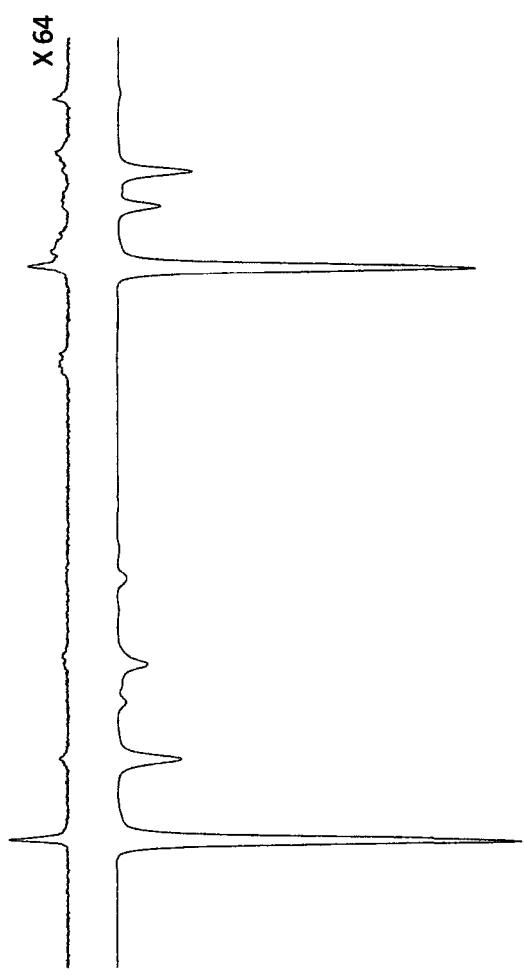
FIG. 9 is a comparison of the $^1$H NMR spectrum collected under Boltzmann conditions (above, with signal multiplied by 64), and the $^1$H NMR spectrum collected under SABRE conditions of a d$_4$-methanol solution containing [IrCl(COD)(IMes)], [Pt(OTf)$_2$(dppp)] and d$_2$-nicotinate.

Addition of para-H$_2$ resulted in the formation of [Ir(H)$_2$(IMes)(nic)$_3$]Cl, which was identified by its characteristic $^1$H NMR hydride signal at δ −22.7. Polarisation transferred into all the aromatic signals corresponding to bound and free pyridazine (FIG. 9), which suggests that the bound nicotinate protons of [Pt(OTf)(nic)(dppp)] [OTf] are enhanced using this method.

Further proof of polarisation transfer into the platinum complex was established through the collection of enhanced $^{31}$P NMR spectra (FIG. 10). Using both 45 and 90° pulses lead to similar enhancements (~5 fold per phosphorus nucleus), but the 90° pulse gave more polarisation on the phosphorus signals that are coupled to platinum.

This d$_4$-methanol solution containing [IrCl(COD)(IMes)], [Pt(OTf)$_2$(dppp)] and d$_2$-nicotinate is stable. After several weeks, there were no signs of degradation by NMR, nor was any precipitate observed to form. This NMR solution mixture was therefore injected into flow apparatus that allows the effect of the polarisation transfer field to be investigated. The aim was to optimise polarisation transfer to phosphorus, however enhanced phosphorus signals were not observed when using the flow apparatus, both at low field (0 and 10G) and at the optimum field used to transfer polarisation to the protons of nicotinate.

The optimum polarisation transfer fields for polarisation transfer to the protons of d$_2$-nicotinate were found to be 40 and 110 G, where each proton was enhanced by ~1000-fold. Interestingly, in between these fields, phase changes were observed in the signals that corresponded to free nicotinate. This resulted in the signal cancelling, as can be seen in FIG. 11, thus although 65 G is typically the optimum polarisation transfer field for the protons of free N-heterocycles, it is not optimum here.

EXAMPLE 6

Metal Complex 2 with d$_2$-nicotinate and [IrCl(COD)(IMes)]

The palladium analogue of the platinum complex was synthesised using the same reaction scheme shown in Scheme 2, but where platinum is now replaced with palladium. As palladium is not NMR active, the T$_1$ values of the phosphorus nuclei in the [Pd(OTf)$_2$(dppp)] complex are predicted to be longer due to less dipole-dipole relaxation.

[IrCl(COD)(IMes)] and [Pd(py)$_2$(dppp)] were dissolved in d$_4$-methanol with 10 equivalents of d$_2$-nicotinate. NMR spectra were collected prior to the addition of para-H$_2$, however the signals in both the $^1$H and $^{31}$P {$^1$H} NMR spectra were broad, presumably due to fast exchange in solution. On addition of para-H$_2$, all of the aromatic signals were enhanced (FIG. 12), and the hydride signal at δ−22.7 (characteristic of [Ir(H)$_2$(IMes)(nic)$_3$]Cl) was observed.

As with the platinum analogue, polarisation transfer into the phosphorus nuclei on the palladium complex was observed when using both a 45° (FIG. 13), and a 90° pulse. There was no obvious difference in the signal enhancements observed on changing the pulse length from 90° to 45°, in both cases the $^{31}$P enhancement was ~7-fold. This enhancement proves that polarisation has transferred from para-H$_2$, to nicotinate, to the phosphorus nuclei in dppp.

Again, over several weeks the sample was stable there was no evidence for degradation in the NMR spectra. A small amount of dark precipitate was observed to form in the NMR tube, however as no free dppp ligand can be detected in the NMR spectra, this could be a small amount of AgCl side-product left over from synthesis. Due to this precipitate, this solution has not been investigated using the flow apparatus.

The maximum enhancement for 1H (standard SABRE process) is at 60 G. Using [IrCl(COD)(IMes)] and [Pd(py)$_2$(dppp)] dissolved in d$_4$-methanol with 10 equivalents of d$_2$-nicotinate a 600-800 fold enhancement was observed (FIG. 14), via flow method at this field. The enhancement for the bound peaks is around 100-folds compared to free-thermal peaks.

REFERENCES

[1] J. H. Ardenkjær-Larsen, B. Fridlund, A. Gram, G. Hansson, L. Hansson, M. H. Lerche, R. Servin, M. Thaning, K. Golman, *Proceedings of the National Academy of Sciences* 2003, 100, 10158-10163.

[2] C. R. Bowers, D. P. Weitekamp, *Journal of the American Chemical Society* 1987, 109, 5541-5542.

[3] T. C. Eisenschmid, R. U. Kirss, P. P. Deutsch, S. I. Hommeltoft, R. Eisenberg, J. Bargon, R. G. Lawler, A. L. Balch, *Journal of the American Chemical Society* 1987, 109, 8089-8091.

[4] K. D. Atkinson, M. J. Cowley, P. I. P. Elliott, S. B. Duckett, G. G. R. Green, J. Lopez-Serrano, A. C. Whitwood, *Journal of the American Chemical Society* 2009, 131, 13362-13368.

[5] R. W. Adams, S. B. Duckett, R. A. Green, D. C. Williamson, G. G. R. Green, *The Journal of Chemical Physics* 2009, 131, 194505.

[6] J. Kurhanewicz, D. B. Vigneron, K. Brindle, E. Y. Chekmenev, A. Comment, C. H. Cunningham, R. J. DeBerardinis, G. G. Green, M. O. Leach, S. S. Rajan, R. R. Rizi, B. D. Ross, W. S. Warren, C. R. Malloy, *Neoplasia* 2011, 13, 81-97.

[7] aM. A. Schroeder, H. J. Atherton, L. C. Heather, J. L. Griffin, K. Clarke, G. K Radda, D. J. Tyler, *Nmr in Biomedicine* 2011, 24, 980-987; bB. Pullinger, H. Profka, J. H. Ardenkjaer-Larsen, N. N. Kuzma, S. Kadlecek, R. R. Rizi, *Nmr in Biomedicine* 2012, 25, 1113-1118; cT. H. Witney, K. M. Brindle, Biochemical Society Transactions 2010, 38, 1220-1224; dE. Y. Chekmenev, J. Hoevener, V. A. Norton, K. Harris, L. S. Batchelder, P. Bhattacharya, B. D. Ross, D. P. Weitekamp, *Journal of the American Chemical Society* 2008, 130, 4212-+.

[8] M. J. Cowley, R. W. Adams, K. D. Atkinson, M. C. R. Cockett, S. B. Duckett, G. G. R. Green, J. A. B. Lohman, R. Kerssebaum, D. Kilgour, R. E. Mewis, *Journal of the American Chemical Society* 2011, 133, 6134-6137.

[9] R. E. Mewis, K. D. Atkinson, M. J. Cowley, S. B. Duckett, G. G. R. Green, R. A. Green, L. A. R. Highton, D. Kilgour, L. S. Lloyd, J. A. B. Lohman, D. C. Williamson, *Magnetic Resonance in Chemistry* 2014, 52, 358-369.

[10] P. Spannring, I. Reile, M. Emondts, P. P. M. Schleker, N. K. J. Hermkens, N. G. J. van der Zwaluw, B. J. A. van Weerdenburg, P. Tinnemans, M. Tessari, B. Blumich, F. Rutjes, M. C. Feiters, *Chemistry—a European Journal* 2016, 9277-9282.

[11] aF. Shi, P. He, Q. A. Best, K. Groome, M. L. Truong, A. M. Coffey, G. Zimay, R. V. Shchepin, K. W. Waddell, E. Y. Chekmenev, B. M. Goodson, *Journal of Physical Chemistry C* 2016, 120, 12149-12156; bM. Fekete, C. Gibard, G. J. Dear, G. G. R. Green, A. J. J. Hooper, A. D. Roberts, F. Cisnetti, S. B. Duckett, *Dalton Transactions* 2015, 44, 7870-7880; cH. F. Zeng, J. D. Xu, M. T. McMahon, J. A. B. Lohman, P. C. M. van Ziji, *Journal of Magnetic Resonance* 2014, 246, 119-121.

The invention claimed is:

1. A method for the preparation of an imaging medium via transfer from a hyperpolarised singlet state that is not parahydrogen, said method comprising the steps of:
   (i) preparing a system containing:
   parahydrogen; a magnetisation transfer complex, with a molecular symmetry that allows the creation of a singlet state between spin pairs within it, the magnetization transfer complex including a reversibly bound small molecule transference substrate;
   applying a magnetic field such that hyperpolarisation is transferred into the magnetization transfer complex, including the reversibly bound small molecule transference substrate;
   (ii) separately or simultaneously introducing a recipient complex capable of binding the small molecule transference substrate, said recipient complex including a recipient substrate, such that the recipient complex and recipient substrate, including the bound transference substrate, is hyperpolarised; and
   (iii) providing an imaging medium by:
   (a) separating the hyperpolarised recipient complex;
   (b) separating the hyperpolarised recipient substrate; or
   (c) separating the bound small molecule transference substrate.

2. A method according to claim 1 wherein the hyperpolarisation is achieved by SABRE.

3. A method according to claim 1 wherein the small molecule transference substrate is characterised by a long lifetime in a low magnetic field.

4. A method according to claim 1 wherein the small molecule transference substrate has a singlet state lifetime that will be 20 seconds or more.

5. A method according to claim 2 wherein the method includes the use of a SABRE hyperpolarisation transfer catalyst.

6. A method according to claim 5 wherein a SABRE hyperpolarisation transfer catalyst is placed in an aqueous phase.

7. A method according to claim 1 wherein parahydrogen (p-$H_2$) gas is added to the system whilst agitating the system.

8. A method according to claim 7 wherein ultrasound is used to agitate the system.

9. A method according to claim 1 wherein the recipient complex contains appropriate $^2H$, Cl or O labels to maximise the relaxation times of the nuclei spins that are to be hyperpolarised.

10. A method according to claim 1 wherein the small molecule transference substrate contains appropriate $^{13}C$ or $^{15}N$ labelling to maximise the proportion of the substrate that can be created in a hyperpolarised NMR visible form in conjunction with appropriate $^2H$, O or Cl labelling to extend their magnetic state lifetimes.

11. A method according to claim 1 wherein the selected small molecule transference substrate contains spin pairs of appropriate $^1H$, $^{13}C$, $^{31}P$, $^{15}N$, $^{29}Si$ or $^{19}F$ labels to enable the formation of long-lived states between corresponding spin pairs within a molecular scaffold that contains appropriate $^2H$ or Cl labelling to extend their lifetime.

12. A method according to claim 1 wherein the small molecule transference substrate contains spin pairs that are homo-nuclear.

13. A method according to claim 1 wherein the small molecule transference substrate contains spin pairs that are selected from $^1H/^1H$ and $^{13}C/^{13}C$.

14. A method according to claim 1 wherein the small molecule transference substrate contains spin pairs that are hetero-nuclear.

15. A method according to claim 6 wherein the hyperpolarisation transfer catalyst is provided with at least one suitable ligation site enabling it to interact with one or more small molecule transference substrates.

16. A method according to claim 15 wherein the hyperpolarisation transfer catalyst comprises an iridium based catalyst.

17. A method according to claim 6 wherein the hyperpolarization transfer catalyst includes iridium with at least one N-heterocyclic carbene (NHC) ligand.

18. A method according to claim 17 wherein the N-heterocyclic carbene (NHC) ligand is selected from:

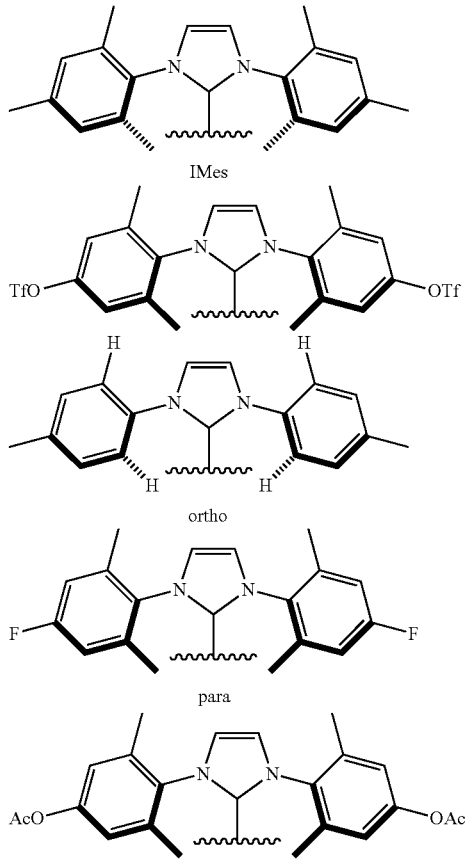

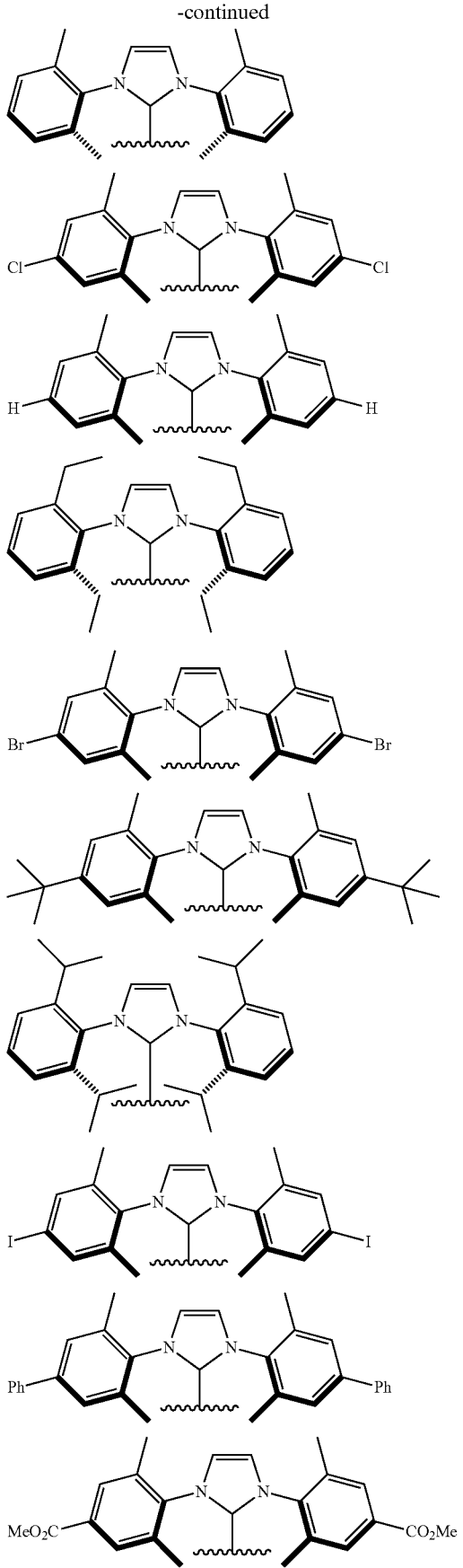
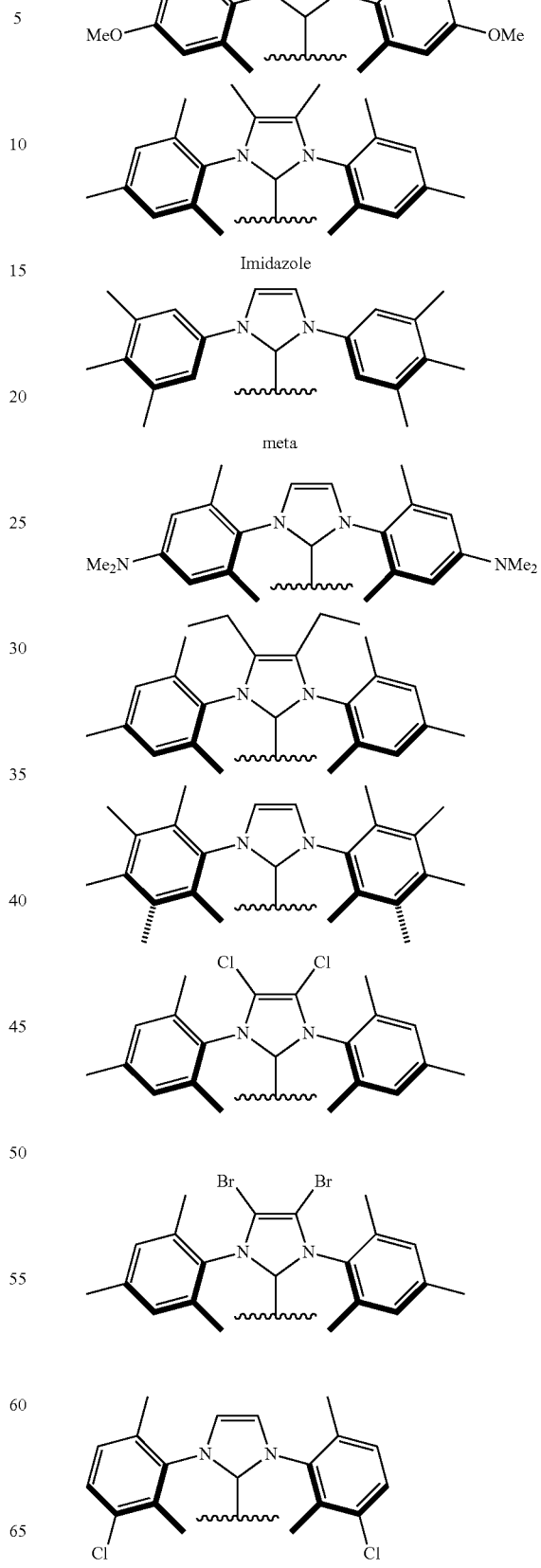

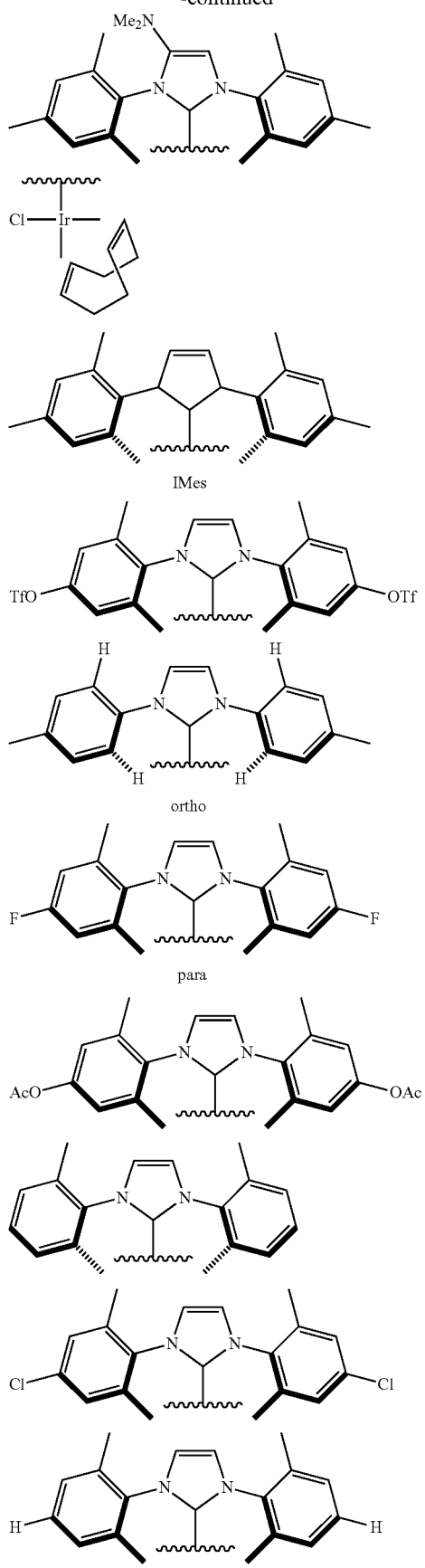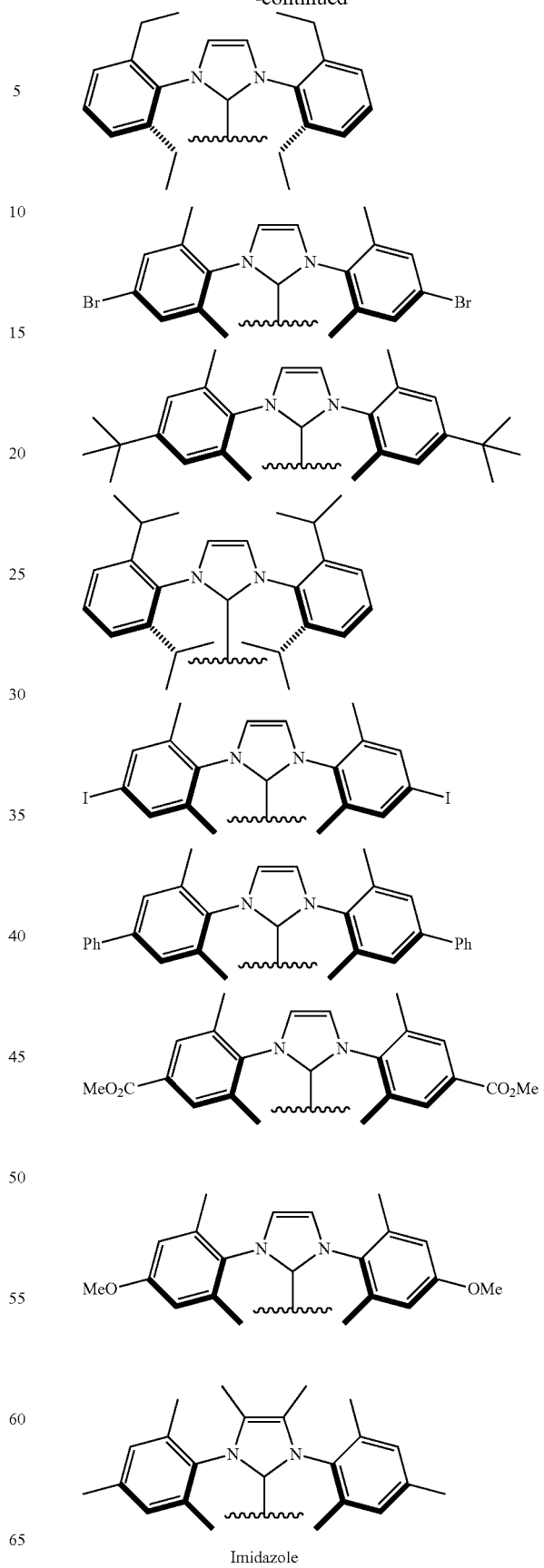

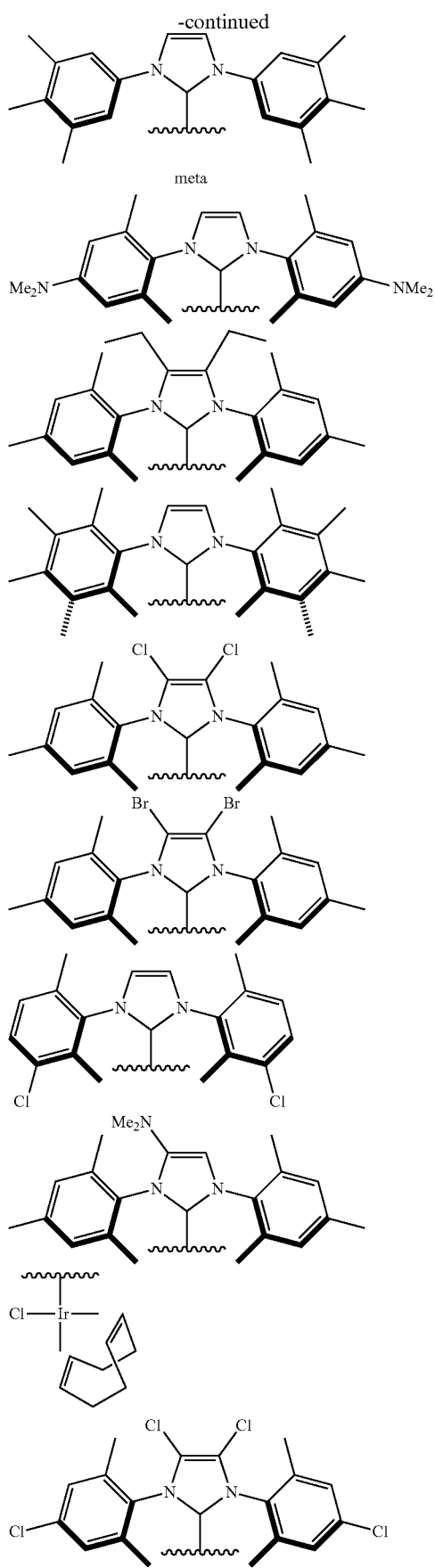
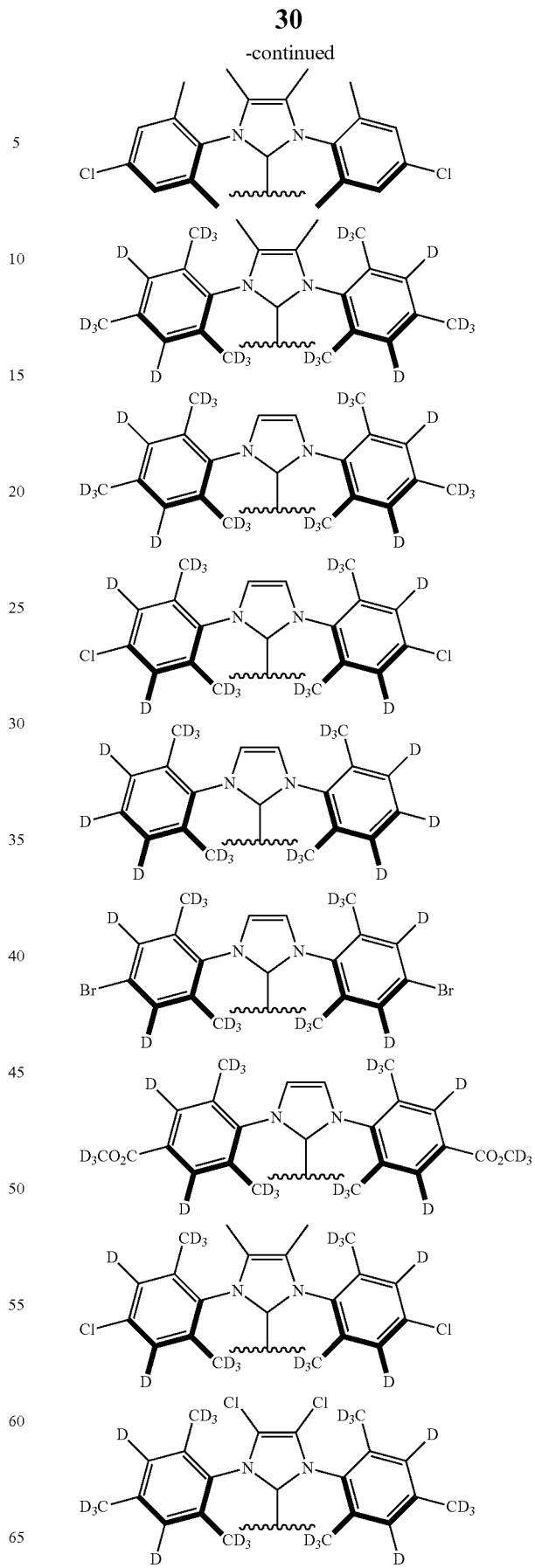

-continued

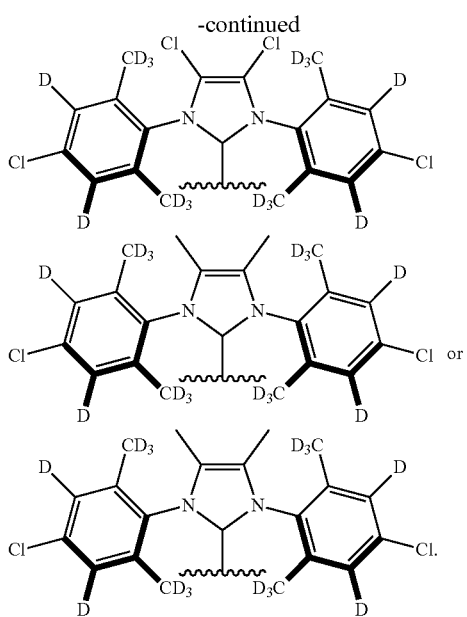

19. A method according to claim 1 wherein the small molecule transference substrate is selected from one or more of pyridine (py), pyridazine (pdz), methyl-pyridazine (methyl-pdz), $d_2$-nicotinate (nic) and $Cl_2$-$d_2$-$^{15}N_2$-pyridazine.

20. A method according to claim 1 wherein a biphasic element is introduced in order to enable the hyperpolarisation transfer process to be completed in a single vessel.

21. A method according to claim 1 wherein the recipient substrate is selected from the group consisting of nicotinamide, nicotine, pyrazine, 5-methyl pyrimidine, acetate, pyruvate, ethoxide, hydroxide, oxalate or gluconate, sugars, glucose, fructose, urea, amides, amino acids, glutamate, glycine, cysteine, aspartate, GABA (γ-aminobutyric acid), nucleotides, vitamins, ascorbic acid, serotonin, penicillin derivatives and sulfonamides.

22. A method of producing a hyperpolarised target substrate imaging medium, said method comprising the steps of:
(i) preparing a system containing a magnetisation transfer complex, said complex including a reversibly bound small molecule transference substrate;
(ii) adding $H_2$ or parahydrogen (p-$H_2$) gas to the system;
(iii) applying a magnetic field such that hyperpolarisation is transferred into the transfer complex, including the reversibly bound small molecule transference substrate;
(iv) separately or simultaneously introducing a recipient complex capable of binding the small molecule transference substrate, said recipient complex including a recipient substrate, such that the recipient complex and recipient substrate, including the bound transference substrate, is hyperpolarised; and
(v) separating the hyperpolarised recipient complex; the hyperpolarised recipient substrate; or the separating the transference substrate to provide a hyperpolarised target substrate imaging medium.

* * * * *